(12) United States Patent
Godavarti et al.

(10) Patent No.: US 7,825,223 B2
(45) Date of Patent: *Nov. 2, 2010

(54) METHODS OF PURIFYING ANTI A β ANTIBODIES

(75) Inventors: Ranganathan Godavarti, Burlington, MA (US); Timothy Iskra, Derry, NH (US)

(73) Assignees: Janssen Alzheimer Immunotherapy, Little Island, County Cork (IE); Wyeth LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/454,772

(22) Filed: Jun. 16, 2006

(65) Prior Publication Data

US 2007/0082367 A1    Apr. 12, 2007

Related U.S. Application Data

(60) Provisional application No. 60/691,821, filed on Jun. 17, 2005.

(51) Int. Cl.
C07K 16/18    (2006.01)
C07K 1/22    (2006.01)

(52) U.S. Cl. .............. 530/388.2; 424/152.1; 424/172.1; 424/177.1; 530/390.5; 530/413

(58) Field of Classification Search .................. None
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 4,851,341 A * | 7/1989 | Hopp et al. ................. | 435/69.7 |
| 5,112,952 A * | 5/1992 | Mallia et al. ............. | 530/387.1 |
| 5,116,964 A | 5/1992 | Capon et al. | |
| 5,223,409 A | 6/1993 | Ladner et al. | |
| 5,225,538 A | 7/1993 | Capon et al. | |
| 5,225,539 A | 7/1993 | Winter | |
| 5,336,603 A | 8/1994 | Capon et al. | |
| 5,428,130 A | 6/1995 | Capon et al. | |
| 5,770,429 A | 6/1998 | Lonberg et al. | |
| 5,786,180 A | 7/1998 | Konig et al. | |
| 6,114,598 A | 9/2000 | Kucherlapati et al. | |
| 6,150,584 A | 11/2000 | Kucherlapati et al. | |
| 6,420,113 B1 | 7/2002 | Buechler et al. | |
| 6,710,226 B1 | 3/2004 | Schenk | |
| 6,743,427 B1 | 6/2004 | Schenk | |
| 6,750,324 B1 * | 6/2004 | Schenk et al. ............ | 530/387.1 |
| 6,761,888 B1 | 7/2004 | Schenk | |
| 6,787,138 B1 | 9/2004 | Schenk | |
| 6,787,139 B1 | 9/2004 | Schenk | |
| 6,787,140 B1 | 9/2004 | Schenk | |
| 6,787,143 B1 | 9/2004 | Schenk | |
| 6,787,144 B1 | 9/2004 | Schenk | |
| 6,787,523 B1 | 9/2004 | Schenk | |
| 6,787,637 B1 | 9/2004 | Schenk et al. | |
| 6,808,712 B2 | 10/2004 | Schenk | |
| 6,818,218 B2 | 11/2004 | Schenk | |
| 6,866,849 B2 | 3/2005 | Schenk | |
| 6,866,850 B2 | 3/2005 | Schenk | |
| 6,870,034 B2 | 3/2005 | Breece et al. | |
| 6,875,434 B1 | 4/2005 | Schenk | |
| 6,890,535 B1 | 5/2005 | Schenk | |
| 6,905,686 B1 | 6/2005 | Schenk | |
| 6,913,745 B1 | 7/2005 | Schenk | |
| 6,936,246 B1 | 8/2005 | Schenk | |
| 6,946,135 B2 | 9/2005 | Schenk | |
| 6,962,707 B2 | 11/2005 | Schenk | |
| 6,972,127 B2 | 12/2005 | Schenk | |
| 6,982,084 B2 | 1/2006 | Schenk | |
| 7,014,855 B2 | 3/2006 | Schenk | |
| 7,179,892 B2 | 2/2007 | Basi | |
| 7,189,819 B2 | 3/2007 | Basi | |
| 7,256,273 B2 | 8/2007 | Basi | |
| 7,575,880 B1 | 8/2009 | Schenk et al. | |
| 7,582,733 B2 | 9/2009 | Basi et al. | |
| 7,588,766 B1 | 9/2009 | Schenk | |
| 7,625,560 B2 | 12/2009 | Basi | |

(Continued)

FOREIGN PATENT DOCUMENTS

EP    0125023 B1    11/1984

(Continued)

OTHER PUBLICATIONS

Definition of "chaotropism". Stedman's Medical Dictionary 27th Edition, Lippincott Williams and Wilkins (2000).*

(Continued)

*Primary Examiner*—David A Saunders
(74) *Attorney, Agent, or Firm*—Alston & Bird LLP

(57) ABSTRACT

The present application provides methods of purifying Aβ binding proteins having a Fc region, for example, anti-Aβ antibodies or antibody fusions, by adsorbing the Aβ binding protein to a Fc binding agent, such as, for example, Protein A or Protein G, followed by a wash with a divalent cation salt buffer to remove impurities and subsequent recovery of the adsorbed Aβ binding protein. The present application also features methods of eluting the purified Aβ binding protein as well as the incorporation of the methods within a purification train. Kits comprising components for carrying out the methods and instructions for use are also provided.

96 Claims, 1 Drawing Sheet

U.S. PATENT DOCUMENTS

| | | | |
|---|---|---|---|
| 7,635,473 | B2 | 12/2009 | Warne et al. |
| 2003/0165496 | A1 | 9/2003 | Basi et al. |
| 2004/0043418 | A1 | 3/2004 | Holtzman et al. |
| 2004/0081657 | A1 | 4/2004 | Schenk |
| 2004/0082762 | A1 | 4/2004 | Basi et al. |
| 2004/0087777 | A1 | 5/2004 | Basi et al. |
| 2004/0192898 | A1 | 9/2004 | Jia et al. |
| 2004/0229330 | A1* | 11/2004 | Bettencourt et al. ......... 435/183 |
| 2005/0013815 | A1 | 1/2005 | Schenk |
| 2005/0019330 | A1 | 1/2005 | Schenk |
| 2005/0059802 | A1 | 3/2005 | Schenk et al. |
| 2005/0090648 | A1 | 4/2005 | Tsurushita et al. |
| 2005/0107594 | A1 | 5/2005 | Sun et al. |
| 2005/0118651 | A1 | 6/2005 | Basi et al. |
| 2005/0142131 | A1 | 6/2005 | Hinton et al. |
| 2005/0169925 | A1 | 8/2005 | Bardroff et al. |
| 2005/0249723 | A1* | 11/2005 | Lazar ...................... 424/133.1 |
| 2006/0029611 | A1 | 2/2006 | Schenk |
| 2006/0034858 | A1 | 2/2006 | Schenk |
| 2006/0099206 | A1 | 5/2006 | Sinacore et al. |
| 2006/0194953 | A1 | 8/2006 | Bonnerjea et al. |
| 2006/0198851 | A1 | 9/2006 | Basi |
| 2006/0210557 | A1 | 9/2006 | Luisi et al. |
| 2007/0072307 | A1* | 3/2007 | Godavarti et al. ........... 436/518 |
| 2007/0082367 | A1 | 4/2007 | Godavarti et al. |
| 2007/0134762 | A1 | 6/2007 | Arumugham et al. |
| 2007/0154480 | A1 | 7/2007 | Schenk et al. |
| 2007/0161088 | A1 | 7/2007 | Arumugham et al. |
| 2008/0096818 | A1 | 4/2008 | Schenk et al. |
| 2008/0145373 | A1 | 6/2008 | Arumugham |
| 2008/0221306 | A1 | 9/2008 | Basi |
| 2008/0227718 | A1 | 9/2008 | Schenk |
| 2008/0279873 | A1 | 11/2008 | Seubert |
| 2008/0292625 | A1 | 11/2008 | Schroeter |
| 2008/0299074 | A1 | 12/2008 | Arumugham |
| 2009/0069544 | A1 | 3/2009 | Basi |
| 2009/0142270 | A1 | 6/2009 | Schroeter et al. |
| 2009/0155256 | A1 | 6/2009 | Black et al. |
| 2009/0191231 | A1 | 7/2009 | Schenk |
| 2009/0285806 | A1 | 11/2009 | Sinacore et al. |
| 2009/0297511 | A1 | 12/2009 | Schenk |

FOREIGN PATENT DOCUMENTS

| | | |
|---|---|---|
| EP | 0323027 A2 | 7/1989 |
| EP | 1601697 B1 | 12/2005 |
| WO | WO 87/02671 A1 | 5/1987 |
| WO | WO 93/08829 A1 | 5/1993 |
| WO | WO-01/62801 A2 | 8/2001 |
| WO | WO-02/46237 A2 | 6/2002 |
| WO | WO 02/46237 A2 | 6/2002 |
| WO | WO-02/088306 A2 | 11/2002 |
| WO | WO-02/088307 A2 | 11/2002 |
| WO | WO-03/015691 A2 | 2/2003 |
| WO | WO-03/016466 A2 | 2/2003 |
| WO | WO-03/070760 A2 | 8/2003 |
| WO | WO-03/077858 A2 | 9/2003 |
| WO | WO-2004/080419 A2 | 9/2004 |
| WO | WO-2004/108895 A2 | 12/2004 |
| WO | WO-2006/066049 A2 | 6/2006 |
| WO | WO-2006/066089 A1 | 6/2006 |
| WO | WO-2006/066171 A1 | 6/2006 |
| WO | WO 2006/138553 A2 | 12/2006 |

OTHER PUBLICATIONS

Q Sepharose Product Instructions [online], [retrieved on Jun. 11, 2007] Retrieved from <http://www6.gelifesciences.com/aptrix/upp00919.nsf/Content/549194A30D280337C1256EB40044A91A/$file/71712800AE.pdf> Published Amersham Biosciences, 2002.*

International Search Report for Application No. PCT/US2006/024026, dated Jun. 17, 2005.

Bales, K.R. et al, "Administration of an Anti-Aβ Fab Fragment to APP$^{V717F}$ Transgenic Mice Reduces Neuritic Plaque," *Therapeutics and Therapeutic Strategies*, Poster Session P4-396, p. S587.

Bard, Frédérique et al, "Epitope and isotype specificities of antibodies to β-amyloid peptide for protection against Alzheimer's disease-like neuropathology," *PNAS*, vol. 100(4):2023-2028 (2003).

Bard, Frédérique et al, "Peripherally administered antibodies against amyloid β-peptide enter the central nervous system and reduce pathology in a mouse model of Alzheimer disease," *Nature Medicine*, vol. 6(8):916-919 (2000).

Bussière, Thierry et al, "Morphological Characterization of Thioflavin-S-Positive Amyloid Plaques in Transgenic Alzheimer Mice and Effect of Passive Aβ Immunotherapy on Their Clearance," *American Journal of Pathology*, vol. 165(3):987-995 (2004).

Buttini, Manuel et al, "β-Amyloid Immunotherapy Prevents Synaptic Degeneration in a Mouse Model of Alzheimer's Disease," *The Journal of Neuroscience*, vol. 25(40):9096-9101 (2005).

Chen, Guiquan et al, "A learning deficit related to age and β-amyloid plaques in a mouse model of Alzheimer's disease," *Nature*, vol. 408:975-979 (2000).

Eliasson, Margareta et al, "Chimeric IgG-binding Receptors Engineered from Staphylococcal Protein A and Streptococcal Protein G," *The Journal of Biological Chemistry*, vol. 263(9):4323-4327 (1988).

Games, Dora et al, "Prevention and Reduction of AD-type Pathology in PDAPP Mice Immunized with Aβ$_{1-42}$," *Ann. NY Acad. Sci.*, vol. 920:274-284 (2000).

Hardy, John, "Amyloid, the presenilins and Alzheimer's disease," *Trends Neurosci.*, vol. 20:154-159 (1997).

Harris, Reed J., "Processing of C-terminal lysine and arginine residues of proteins isolated from mammalian cell culture," *Journal of Chromatography A*, vol. 705:129-134 (1995).

Johnson-Wood, K. et al, "Amyloid precursor protein processing and Aβ$_{42}$ deposition in a transgenic mouse model of Alzheimer's disease," *Proc. Natl. Acad. Sci. USA*, vol. 94:1550-1555 (1997).

Kajkowski, Eileen M. et al, "β-Amyloid Peptide-induced Apoptosis Regulated by a Novel Protein Containing a G Protein Activation Module," *The Journal of Biological Chemistry*, vol. 276(22):18748-18756 (2001).

Koh, Jae-young et al, "β-Amyloid protein increases the vulnerability of cultured cortical neurons to excitotoxic damage," *Brain Research*, vol. 533:315-320 (1990).

Köhler, G. et al, "Continuous cultures of fused cells secreting antibody of predefined specificity," *Nature*, vol. 256:495-497 (1975).

Kostelny, Sheri A. et al, "Formation of a Bispecific Antibody by the Use of Leucine Zippers," *The Journal of Immunology*, vol. 148:1547-1553 (1992).

Lorenzo, A. et al, "Amyloid Fibril Toxicity in Alzheimer's Disease and Diabetes," *Ann. NY Acad. Sci.*, vol. 777:89-95 (1996).

Mattson, Mark P. et al, "β-Amyloid Peptides Destabilize Calcium Homeostasis and Render Human Cortical Neurons Vulnerable to Excitotoxicity," *The Journal of Neuroscience*, vol. 12(2):376-389 (1992).

Selkoe, Dennis J., "Amyloid β Protein Precursor and the Pathogenesis of Alzheimer's Disease," *Cell*, vol. 58:611-612 (1989).

Sikkema, W. Dirk, "An Fc-binding protein," *Amer. Biotech. Lab.*, vol. 7:42 (1989).

Songsivilai, S. et al, "Bispecific antibody: a tool for diagnosis and treatment of disease," *Clin. exp. Immunol.*, vol. 79:315-321 (1990).

Walsh, Dominic M. et al, "Naturally secreted oligomers of amyloid β protein potently inhibit hippocampal long-term potentiation in vivo," *Nature*, vol. 416:535-539 (2002).

Zameer, Andleeb et al, "Single Chain Fv Antibodies against 25-35 Peptide Fragment of Amyloid-β: Potential Therapeutic for Alzheimers Disease," *Therapeutics and Therapeutic Strategies*, Poster Session P4-420, p. S593.

International Preliminary Report on Patentability for Application No. PCT/US2006/024026, dated Dec. 17, 2007.

Hay et al. "Bacteriophage cloning and *Escherichia coli* expression of a human IgM Fab," *Hum. Antibod. Hybridomas*, vol. 3;81-85 (1992).

Hoogenboom et al. "Multi-subunit proteins on the surface of filamentous phage: methodologies for displaying antibody (Fab) heavy and light chains," *Nucleic Acids Research*, vol. 19(15):4133-4137 (1991).

Liu et al. "Chimeric mouse-human IgG1 antibody that can mediate lysis of cancer cells," *Proc. Natl. Acad. Sci. USA*, vol. 84:3439-3443 (1987).

Milstein et al, "Hybrid hybridomas and their use in immunohistochemistry," *Nature*, vol. 305:537-540 (1983).

Oi et al, "Chimeric Antibodies," *BioTechniques*, vol. 4(3):214-221 (1986).

PCT International Preliminary Report on Patentability of Dec. 17, 2007 with Written Opinion for application PCT/US2006/023478.

PCT Search Report of Dec. 29, 2006 for application PCT/US2006/023478.

Traunecker et al, "Bispecific single chain molecules (Janusins) target cytotoxic lymphocytes on HIV infected cells," *The EMBO Journal*, vol. 10(12):3655-3659 (1991).

U.S. Appl. No. 11/455,203, Office Action mailed Jun. 30, 2009.

U.S. Appl. No. 11/455,203, Office Action mailed Jul. 17, 2008.

U.S. Appl. No. 11/455,203, Office Action mailed Apr. 9, 2008.

Amersham Biosciences, "Antibody Purification, Handbook," retrieved online at www.chromatrography.amershambiosciense.com (2002).

U.S. Appl. No. 11/455,203, Final Office Action mailed Nov. 18, 2009.

* cited by examiner

METHODS OF PURIFYING ANTI A β ANTIBODIES

RELATED APPLICATIONS

This application claims priority to U.S. provisional patent application "METHODS OF PURIFYING Fc REGION CONTAINING PROTEINS", filed Jun. 17, 2005 having Ser. No. 60/691,821. The entire content of this application is incorporated herein.

BACKGROUND OF THE INVENTION

Alzheimer's disease ("AD") is a neurodegenerative disorder characterized by the occurrence of amyloid plaques, neurofibrillary tangles and significant neuronal loss. β-Amyloid protein (also referred to as the Aβ peptide), the main component of senile plaques, has been implicated in the pathogenesis of Alzheimer's disease (Selkoe (1989) *Cell* 58:611-612; Hardy (1997) *Trends Neurosci.* 20:154-159). β-Amyloid has been shown to be both directly toxic to cultured neurons (Lorenzo and Yankner (1996) *Ann. NY Acad. Sci.* 777:89-95) and indirectly toxic through various mediators (Koh et al. (1990) *Brain Research* 533:315-320; Mattson et al. (1992) *J. Neurosciences* 12:376-389). Additionally, in vivo models, including the PDAPP mouse and a rat model have linked β-amyloid to learning deficits, altered cognitive function, and inhibition of long-term hippocampal potentiation (Chen et al. (2000) *Nature* 408:975-985; Walsh et al. (2002) *Nature* 416:535-539). Therefore, a great deal of interest has focused on therapies that alter the levels of β-amyloid to potentially reduce the severity or even abrogate the disease itself.

One AD treatment strategy that has recently emerged in response to successful studies in PDAPP mouse and rat experimental models, is that of passive immunization of individuals to provide immunoglobulins such as antibodies specific to β-amyloid. (See e.g., Bard et al. (2000) *Nat. Med.* 6:916-919 and Bard et al. (2003) *Proc. Natl. Acad. Sci. USA* 100:2023-2028). Recently, it has also been shown that Abeta reduction by passive immunization protects against the progressive loss of synaptic degeneration in a transgenic mouse model of Alzheimer's disease. (Buttini et al. (2005) *J. Neurosci.* 25:9096-101).

Recent advances in recombinant technology have allowed for the production of antibodies against virtually any target, for example, cancer cells, bacteria, and viruses. Typically, an antibody is produced using a cell line that has been engineered to express the antibody at high levels. The engineered cell line is subsequently grown in a culture that comprises a complex mixture of sugars, amino acids, and growth factors, as well as various proteins, including for example, serum proteins. However, separation of complete antibodies from cell by-products and culture components to a purity sufficient for use in research or as therapeutics poses a formidable challenge. The purification of the antibody molecules is especially critical if the antibodies are to be used as a drug for administration to humans.

Traditional antibody purification schemes (or trains) often comprise a chromatography step which exploits an ability of the antibody molecule to preferentially bind or be retained by the solid phase (or functionalized solid phase) of a chromatography column compared to the binding or retention of various impurities. Schemes have been proposed or carried out to purify antibodies which first bind CH2/CH3 region-containing proteins to Protein A immobilized on a solid phase, followed by removal of impurities bound to the solid phase by washing the solid phase with a hydrophobic electrolyte solvent and the subsequent recovery of the CH2/CH3 region-containing proteins from the solid phase. However, these schemes are limited in that the conditions used to preferentially bind the CH2/CH3 region-containing proteins also support binding of impurities (e.g., antibodies with incomplete CH2/CH3 regions). In the development of human therapeutics, such impurities are highly undesirable.

Accordingly, a need exists for improvements in the purification of proteins or polypeptides having constant regions, in particular, proteins having Fc regions (e.g., antibodies), produced in cell culture.

SUMMARY OF THE INVENTION

The present invention features methods of purifying Aβ-binding proteins, in particular, Aβ-binding antibodies. The methods of the invention are especially suited for purification of proteins (e.g., antibodies) developed for administration to humans. In particular, the invention features the purification of proteins having constant regions, in particular, proteins having Fc regions (e.g., antibodies), produced in cell culture.

In various aspects, the present invention features methods for separating an Aβ0 binding protein having an Fc region, such as an anti-Aβ antibody, from a source liquid comprising the protein and one or more impurities. In the methods of the invention, the Aβ binding protein is adsorbed to an Fc binding agent and then the Fc binding agent is washed with a buffer solution containing a divalent cation salt to remove one or more impurities. The protein is then recovered from the Fc binding agent in an elution solution. The methods of the invention are particularly useful for removing impurities such as intron read through variant species (IRT), under disulfide bonded species (UDB) and/or low molecular weight variant species (LMW). The methods of the invention also are effective in removing impurities such as host cell proteins (HCP) and DNA.

The methods of the present invention comprise one or more chromatographic separation steps and in addition can comprise one or more filtration steps. The chromatographic separation steps can be continuous or discontinuous (e.g., a batch approach), or a combination of both. In various embodiments, the methods comprise one or more filtration steps, for example, to remove viruses, concentrate and buffer the solution containing the target protein, and to remove microbial contaminants.

In various embodiments, the anti-Aβ antibody is a murine antibody, a chimeric antibody, a humanized antibody or a human antibody. In some embodiments, the anti-Aβ antibody is an antibody that specifically binds to epitope within residues 1-7, 1-5, 3-7, 3-6, 13-28, 15-24, 16-24, 16-21, 19-22, 33-40, 33-42 of Aβ. Exemplary anti Aβ antibodies specifically bind to an epitope within residues 1-10 of Aβ, such as, for example, within residues 1-7, 1-5, 3-7, or 3-6 of Aβ. Other exemplary anti Aβ antibodies specifically bind to an epitope within residues 13-28 of Aβ, such as, for example, within residues 16-21 or 19-22 of Aβ. Yet other exemplary anti Aβ antibodies specifically bind to a C terminal epitope of Aβ such as, for example, 33-40 or 33-42 of Aβ. In some embodiments, the anti Aβ antibody binds a discontinuous epitope which includes residues within 1-7 and within 13-28 of Aβ. Other embodiments feature Fab, Fab'(2) or Fv fragments of anti-Aβ antibodies. In some such embodiments, the antibody is bispecific antibody or an antibody made by the process described in International Patent Publication No. WO03/070760.

In a preferred embodiment, the antibody is a humanized anti-Aβ antibody, and in certain embodiments, is an anti-Aβ antibody selected from the group consisting of 3D6, 10D5, 12B4, 12A11, 15C11 and 266. The isotype of the antibody can be IgM, IgG1, IgG2, IgG3, IgG4 or any other pharmaceutically acceptable isotype. In preferred embodiments, the isotype is human IgG1 or human IgG4.

In various embodiments, the Aβ binding protein is recombinantly produced. In various embodiments, the Aβ binding protein is recombinantly produced in a Chinese Hamster Ovary (CHO) cell.

In various embodiments, the one or more impurities comprise one or more of a host cell protein, a host cell DNA, a cell culture protein, an undesired species of the Aβ binding protein, and mixtures thereof. For example, in various embodiments, the undesired species of the Aβ binding protein comprises one or more of antibody chains or fragments thereof having intron read through sequence, one or more antibody chains or fragments thereof having an improper disulfide linkage, a half-antibody or fragment thereof, a light chain dimer or fragment thereof, and a heavy chain dimer or fragment thereof.

In one aspect, the methods of the present invention purify an Aβ binding protein, preferably an anti-Aβ antibody, from a source liquid comprising the protein and one or more impurities by first adsorbing the protein to an Fc binding agent, followed by washing the Fc binding agent with a buffer solution containing a divalent cation salt to remove one or more impurities, and subsequently recovering the protein from the Fc binding agent. In various embodiments, the steps of adsorbing the protein to an Fc binding agent and washing the Fc binding agent with a buffer solution containing a divalent cation salt, are performed at temperature in the range between about 2° C. to about 24° C. In various embodiments, the step of recovering the protein from the Fc binding agent comprises eluting the protein using an elution buffer having a pH in the range from about 2.0 to about 6.5.

In various embodiments, the Fc region binding agent comprises one or more of Protein A and Protein G. In a preferred embodiment, the Fc binding agent is immobilized on a solid phase. This solid phase can comprise, for example, one or more of a bead, an agarose matrix, silica, and mixtures thereof.

The divalent cation salt present in the buffer that is used to wash the Fc binding agent can comprise, for example, a chaotropic salt. Suitable divalent cation salts for preparation of the wash buffer solution include, but are not limited to, magnesium chloride, calcium chloride, nickel chloride and mixtures thereof. In various embodiments, suitable divalent cation salts for preparation of the wash buffer solution include, but are not limited to, thiocyanate ($SCN^-$), perchlorate ($ClO_4^-$), nitrate ($NO_3^-$), chloride, and bromide salts of divalent group II (e.g., magnesium, calcium, barium, etc.) cations, divalent transition metal (e.g., copper, nickel, manganese, etc.) cations, and combinations of these salts.

In various embodiments, the buffer solution containing the divalent cation salt has a pH value in the range between about 4 to about 9, and in some embodiments, between about 4 to about 8, between about 4.5 to about 7.5 or between about 6 to about 8. Values and ranges included and/or intermediate within the ranges set forth herein are also intended to be within the scope of the present invention. For example, the divalent cation salt has a pH value between about 7.1 to about 7.9, between about 7.2 to about 7.9, between about 7.3 to about 7.7, between about 7.4 to about 7.6, between about 4 to about 5, between about 5 to about 6, between about 6 to about 7, or between about 8 to about 9.

Moreover, ranges having values recited herein as an upper or lower limit are intended to be within the scope of the present invention. For example, the divalent cation salt has a pH of at least about (or about) 4.5, 5, 5.5, 6, 6.5, 7, 7.5, or 8.

In various embodiments, the buffer solution has a divalent cation salt concentration in the range between about 0.1 M to about 5 M, and in some embodiments between about 0.5 M to about 3M, between about 1.0 M to about 3 M or between about 0.6 M to about 2.5 M. For example, the divalent cation buffer may comprise at least about 0.6 M $CaCl_2$, or at least about 2M $MgCl_2$ or at least about 2M $CaCl_2$. Values and ranges included and/or intermediate within the ranges set forth herein are also intended to be within the scope of the present invention. For example, the buffer solution has a divalent cation salt concentration between about 0.5 M to about 0.75 M, between about 0.5 M to about 0.8 M, between about 0.5 M to about 0.9 M, between about 0.5 M to 1.0 M, between about 0.5 M to 2 M, between about 1.5 M to about 2.0 M, between about 1.5 M to about 2.5 M, between about 1.5 M to about 3.0 M, or between about 2.5 M to about 3 M.

Moreover, ranges having values recited herein as an upper or lower limit are intended to be within the scope of the present invention. For example, the buffer solution has a divalent cation salt concentration of at least about (or about) 0.6 M, 1 M, 1.5 M, 2 M, 2.5 M, or 3 M. In various embodiments, the buffer solution containing a divalent cation salt has a temperature in the range between about 2° C. to about 24° C.

In various embodiments, the step of recovering the antibody from the Fc binding agent comprises eluting the antibody using an elution buffer having a pH in the range of about 2.0 to about 6.5, preferably in the range of about 2.0 to about 4.0, more preferably in the range of about 2.5 to about 3.5. Values and ranges included and/or intermediate within the ranges set forth herein are also intended to be within the scope of the present invention. For example, the elution buffer has a pH of between about 2 to about 3 or between about 3 to about 4.

Moreover, ranges having values recited herein as an upper or lower limit are intended to be within the scope of the present invention. For example, the elution buffer has a pH of at least about (or about) 2, 2.5, 3, 3.5 or 4.

In various embodiments, the recovered proteins can be subjected to additional purification steps either prior to, or after, the Fc binding agent chromatography step. For example, exemplary further purification steps include, but are not limited to: anion exchange chromatography, cation exchange chromatography, immobilized metal affinity chromatography, hydrophobic interaction chromatography (HIC), hydroxyapatite chromatography, dialysis, affinity chromatography, ammonium sulphate precipitation, ethanol precipitation, reverse phase HPLC (RP-HPLC), chromatofocusing, ultrafiltration, diafiltration, microfiltration, and gel filtration. In various embodiments, the Fc binding agent chromatography step is followed by an anion exchange chromatography and a HIC step. In various embodiments, the chromatography steps are further followed by a virus filtration step, an ultrafiltration/diafiltration step, and/or a microbial contaminant filtration step.

In one aspect, the present invention provides methods for purifying an Aβ binding protein, preferably an anti-Aβ antibody, from an impurity-containing solution thereof. In various embodiments, the methods comprise first adsorbing the protein to an Fc binding agent, followed by washing the Fc binding agent with a buffer solution containing a divalent cation salt to remove one or more impurities, and subsequently recovering the protein from the Fc binding agent to produce a first eluent pool.

In various embodiments, the purification process continues with subjecting the first eluent pool to ion exchange chromatography by contacting an ion exchange resin with the first eluent pool such that the target protein does not adsorb to the resin and recovering the flow-through target protein to produce a second eluent pool. In various embodiments, the ion exchange chromatography step further comprises washing the ion exchange resin with a buffered wash solution to recover at least a portion of any adsorbed target protein.

In various embodiments, the purification process continues with subjecting the second eluent pool to hydrophobic interaction chromatography by adsorbing the target protein to a hydrophobic interaction resin (e.g., a solid phase functionalized with hydrophobic ligands), washing the hydrophobic interaction resin with a buffered wash solution with an ionic strength which does not substantially elute the target protein and recovering the purified target protein (typically using an elution buffer with an ionic strength low enough to desorb the target protein from the hydrophobic interaction resin).

In preferred embodiments of the various aspects of the inventions, the Fc binding agent is immobilized on a solid phase, which is preferably equilibrated with a suitable buffer prior to contact with the source liquid. The solid phase is preferably a column comprising agarose immobilizing the Fc binding agent. In various embodiments, the column is coated with a reagent, such as glycerol, to decrease or prevent non-specific adherence to the column.

In various embodiments, the proteins purified by methods of the present invention can be formulated in a pharmaceutically acceptable carrier and used for various diagnostic, therapeutic or other uses known for such molecules.

In various aspects, the present invention provides methods for purifying an Aβ binding protein, preferably an anti-Aβ antibody, from a solution containing the protein and intron read-through variants (IRT) thereof. In featured aspects, methods of the present invention are used to reduce the levels of one or more intron read-through variant species in a protein preparation, for example, in an antibody preparation. In various embodiments, the protein recovered from the Fc binding agent has a level of intron read-through variants that is at least 5 fold less than the level of intron read-through variants in the source liquid, and in some embodiments at least 10 fold less than the level of intron read-through variants in the source liquid. In various embodiments, the intron read-through variants comprise less than about 1.0%, 0.8%, 0.5%, 0.2% or 0.1% of the species of said protein in the solution containing said protein recovered from the Fc binding agent.

In various aspects, the present invention provides methods for purifying an Aβ binding protein, preferably an anti-Aβ antibody, from a solution containing the protein and low molecular weight variants (LMW) thereof. In featured aspects, methods of the present invention are used to reduce the levels of one or more low molecular weight variant species in a protein preparation, such as an antibody preparation. In various embodiments, the protein recovered from the Fc binding agent has a level of low molecular weight variants that is at least 5 fold less than the level of low molecular weight variants in the source liquid, and in some embodiments at least 10 fold less than the level of low molecular weight variants in the source liquid. In various embodiments, the low molecular weight variants comprise less than about 1.0%, 0.8%, 0.5%, 0.2% or 0.1% of the species of said protein in the solution containing said protein recovered from the Fc binding agent.

In various aspects, the present invention provides methods for purifying an Aβ binding protein, preferably an anti-Aβ antibody, from a solution containing the protein and under disulfide bonded variants (UDB) thereof. In featured aspects, methods of the present invention are used to reduce the levels of one or more under disulfide bonded variant species in a protein preparation, such as an antibody preparation. In various embodiments, the protein recovered from the Fc binding agent has a level of under disulfide bonded variants that is at least 5 fold less than the level of under disulfide bonded variants in the source liquid, and in some embodiments at least 10 fold less than the level of under disulfide bonded variants in the source liquid. In various embodiments, the under disulfide bonded variants comprise less than about 20%, 15%, 10%, 5%, 2% or 1% of the species of said protein in the solution containing said protein recovered from the Fc binding agent.

In another aspect, the present invention provides an Aβ binding protein, preferably an anti-Aβ antibody, purified according to any of the methods that comprise at least the steps of first adsorbing the protein to an Fc binding agent, followed by washing the Fc binding agent with a buffer solution containing a divalent cation salt to remove one or more impurities, and subsequently recovering the protein from the Fc binding agent. In various embodiments, the anti-Aβ antibody is a humanized anti-Aβ antibody selected from the group consisting of 3D6, 10D5, 12B4, 12A11, 15C11 and 266. In various embodiments, the anti-Aβ antibody is a humanized anti-Aβ antibody selected from the group consisting of 3D6, 10D5, 12B4, and 12A11.

In another aspect, the present invention provides a system suitable for performing any of the methods that comprise at least the steps of first adsorbing the Aβ binding protein that has an Fc region, such as an anti-Aβ antibody, to an Fc binding agent, followed by washing the Fc binding agent with a buffer solution containing a divalent cation salt to remove one or more impurities, and subsequently recovering the protein from the Fc binding agent.

In another aspects, the present invention provides a purification train for performing any of the methods that comprise at least the steps of first adsorbing the Aβ binding protein, preferably an anti-Aβ antibody, to an Fc binding agent, followed by washing the Fc binding agent with a buffer solution containing a divalent cation salt to remove one or more impurities, and subsequently recovering the protein from the Fc binding agent.

The present invention also features, in various aspects, kits for use in performing one or more of the methods of the present invention. In various embodiments, the kit comprises at least one reagent and instructions for use of the kit. For example, a kit can comprise one or more reagents such as an Fc binding agent, a divalent cation salt and reagents for the preparation of buffer wash solution containing a divalent cation salt, along with instructions for use of the kit, e.g, to purify an Aβ binding protein, e.g., anti-Aβ antibody.

DETAILED DESCRIPTION OF THE INVENTION

Figure 1:
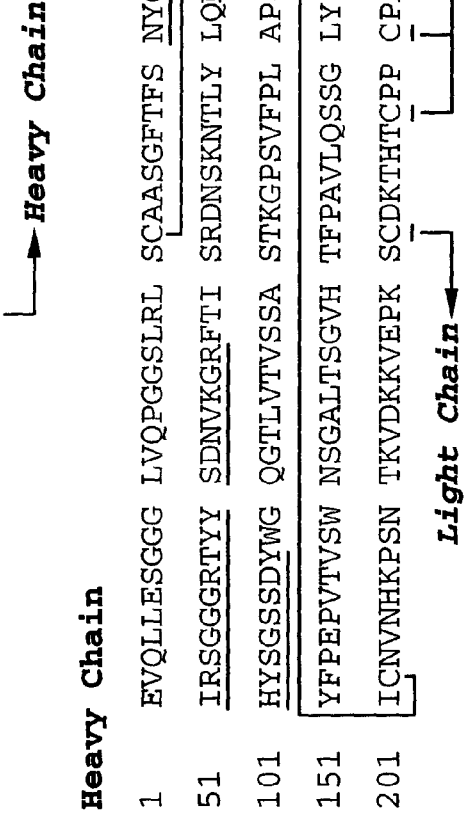
FIG. 1 shows the complete amino acid sequences of the humanized 3D6 version2 (hu3D6.v2) anti Aβ antibody light and heavy chains, SEQ ID NO1 and SEQ ID NO:2, respectively. Light chain complementarity determining regions (CDR), i.e., CDR1, CDR2, and CDR3 are, respectively, at residue positions 24-39, 55-61, and 94-102 (upper panel). Heavy chain complementarity determining regions (CDR), i.e., CDR1, CDR2, and CDR3 are, respectively, at residue positions 40-44, 50-65, and 99-108 (lower panel). Predicted intramolecular disulfide bonds are illustrated by connections of the cysteine residues involved. Cysteines expected to form intermolecular disulfide bonds are underlined and the connectivity indicated. The N-linked glycosylation consensus site of the antibody heavy chain is indicated in italics at residue positions 299-301 (lower panel). The predicted heavy chain C-terminal lysine is shown in parenthesis.

Prior to further describing the invention, it may be helpful to an understanding thereof to set forth definitions of certain terms to be used herein. The definitions set forth herein have been grouped for ease of reference only and not by way of limitation.

Protein Related Definitions

The present invention features methods of purifying Aβ-binding proteins, in particular, Aβ-binding antibodies. In particular, the invention features the purification of proteins having constant regions, in particular, proteins having Fc regions (e.g., antibodies), produced in cell culture. In various aspects, the present invention provides methods for purifying an Aβ binding protein that contains an Fc region, such as an anti-Aβ antibody, from a solution containing the protein and one or more read-through variants thereof, such as, for example, intron read-through variants. In featured aspects, methods of the present invention are used to reduce the levels of one or more intron read-through (IRT) variant species in a protein preparation, for example, in an antibody preparation. The terms "intron read-through variant," and "intron read-through variant species" are used interchangeably herein and refer to the product of a process where, in the synthesis of the Aβ binding protein, polypeptide chain elongation is terminated prior to transcription of a coding region by a stop codon in the intron prior to the coding region. The result is a variant of the protein of interest (i.e., an intron read-through variant) with one or more incomplete or missing domains. Such introns can contain more than one stop codon resulting in the possibility of producing several different intron read-through variants.

The term "under disulfide bonded variant" (or "UDB") refers to any species where at least one disulfide bond is missing. The missing disulfide bond can be either an interchain disulfide bond or an intrachain disulfide bond or a combination of the two.

The term "low molecular weight species" or "LMW" species refers to variants of the Aβ binding protein, e.g., anti-Aβ antibody, including a protein species that consists of free heavy chain, free light chain, IRT species, half-molecule, and three-quarters-molecule, or mixtures thereof.

Protein A is an about 42 kD cell wall protein found in most strains of *Staphylococcus aureas* which binds with high affinity (about $10^{-8}$ M to human IgG) to the Fc region of antibodies. As used herein, the term "Protein A" encompasses Protein A recovered from a native source thereof, Protein A produced synthetically (e.g., by peptide synthesis, by recombinant techniques, etc.), and variants thereof which retain the ability to bind proteins which have a CH2/CH3 region.

Protein G is a cell wall protein from group G streptococci. Protein G is a type III Fc-receptor which binds with high affinity to the Fc region of antibodies, in particular, IgG antibodies. As used herein, the term "Protein G" encompasses Protein G recovered from a native source thereof, Protein G produced synthetically (e.g., by peptide synthesis, by recombinant techniques, etc.), and variants thereof, which retain the ability to bind proteins which have a Fc region.

The terms "β-amyloid protein", "β-amyloid peptide", "β-amyloid", "Aβ" and "Aβ peptide" are used interchangeably herein.

The term "Aβ binding protein" as used herein is intended to refer to a protein capable of specifically binding to Aβ peptide(s) or to epitopes(s) within said Aβ peptide(s), or having an appreciable binding affinity for Aβ. In exemplary embodiments, the Aβ binding protein contains an Fc region such that it can bind an Fc binding agent according to the methods of the invention.

The term "antibody" or "immunoglobulin" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains. The term "antibody" or "immunoglobulin" includes monoclonal antibodies (including full length monoclonal antibodies), polyclonal antibodies, multispecific antibodies (for example, bispecific antibodies), chimeric antibodies, CDR-grafted antibodies, humanized antibodies, human antibodies, and single chain antibodies (scFvs). The term "monoclonal antibody" or "monoclonal antibody composition", as used herein, refers to a population of antibody molecules that contain only one species of an antigen binding site capable of recognizing and binding to a particular epitope of a target antigen, for example, an epitope(s) of Aβ. A monoclonal antibody composition thus typically displays a single binding specificity and affinity for a particular target antigen with which it immunoreacts. Non-human antibodies can be "humanized" by techniques described, for example, in U.S. Pat. No. 5,225,539. In one method, the non-human CDRs are inserted into a human antibody or consensus antibody framework sequence. Further changes can then be introduced into the antibody framework to modulate affinity or immunogenicity.

The term "anti-Aβ antibody" is intended to refer to an antibody having binding specificity for an Aβ peptide of human amyloid precursor protein (APP). Aβ peptide is also known in the art as beta amyloid peptide. Aβ peptide is an approximately 4 kD internal fragment of 39-43 amino acids of APP ($A\beta_{39}$, $A\beta_{40}$, $A\beta_{41}$, $A\beta_{42}$ and $A\beta_{43}$, respectively). The term "anti-Aβ antibody" is intended to encompass antibodies having binding specificity for any of these forms of Aβ peptide. Specific anti-Aβ antibodies of interest include, but are not limited to, 3D6, 10D5, 12B4, 12A11, 15C11 and 266, and humanized versions thereof. Exemplary anti-Aβ antibodies are described in U.S. application Ser. No. 10/010,942, filed Dec. 6, 2001 (U.S. Patent Publication No. 20030165496A1; see also PCT Publication No. WO 2002/46237A2); U.S. application Ser. No. 10/388,389, filed Mar. 12, 2003 (U.S. Patent Publication No. 20040087777A1; see also PCT Publication No. WO 2004/080419A2); U.S. application Ser. No. 10/388,214, filed Mar. 12, 2003 (U.S. Patent Publication No. 20040082762A1; see also PCT Publication No. WO 2003/077858A2); U.S. application Ser. No. 10/858,855, filed Jun. 1, 2004 (U.S. Patent Publication No. 20050118651A1; see also PCT Publication No. WO 2004/108895A2); and U.S. application Ser. No. 11/304,986, filed Dec. 15, 2005; see also PCT/US05/45515); the entire contents of all of which are hereby incorporated by reference.

Additional exemplary anti-Aβ antibodies are described in U.S. application Ser. No. 10/226,435, filed Feb. 26, 2001 (U.S. Patent Publication No. 20040043418A1; see also PCT Publication No. WO01/062801A2), U.S. application Ser. No. 10/487,322, filed Aug. 14, 2002 (U.S. Patent Publication No. 20040192898A1; see also PCT Publication No. WO03/016466A2); U.S. application Ser. No. 10/476,265, filed Apr. 26, 2002 (U.S. Patent Publication No. 20050090648A1; see also PCT Publication No. WO02/088306A2); U.S. application Ser. No. 10/497,475, filed Apr. 26, 2002; (U.S. Patent Publication No. 20050142131A1; see also PCT Publication No. WO02/088307A2); and U.S. application Ser. No. 10/505, 313, filed Feb. 20, 2003; (U.S. Patent Publication No. 20050169925; see also PCT Publication No. WO03/070760A2).

The term "antibody fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. Methods for the construction of Fab fragments are described, for example, Huse, et al. (1989) Science 246: 1275 1281). Other antibody fragments may be produced by techniques known in the art including, but not limited to: (i) an F(ab')2 fragment produced by pepsin digestion of an antibody molecule; (ii) a Fab fragment generated by reducing the disulfide bridges of an F(ab')2 fragment; (iii) a Fab' fragment generated by the treatment of the antibody molecule with papain and a reducing agent and (iv) Fv fragments. The term "antigen-binding fragment" refers to a polypeptide fragment of an immunoglobulin or antibody that binds antigen or competes with the intact antibody from which they were derived for specific antigen binding.

The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). "Variable" domains on the light chain are referred to interchangeably as "light chain variable regions", "light chain variable domains", "VL" regions or "VL" domains). "Variable" domains on the heavy chain are referred to interchangeably as "heavy chain variable regions", "heavy chain variable domains", "VH" regions or "VH" domains).

The term "region" can also refer to a part or portion of an antibody chain or antibody chain domain (for example, a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide, such as, for example, an antibody, antibody chain, domain or region thereof. For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "specific binding" of an antibody means that the antibody exhibits appreciable affinity for a particular antigen or epitope and, generally, does not exhibit significant cross-reactivity. In exemplary embodiments, the antibody exhibits no cross-reactivity (for example, does not cross-react with non-Aβ peptides or with remote or distant epitopes on Aβ). "Appreciable" or preferred binding includes binding with an affinity of at least $10^{-6}$, $10^{-7}$, $10^{-8}$, $10^{-9}$ M, or $10^{-10}$ M. Affinities greater than $10^{-7}$ M, preferably greater than $10^{-8}$ M are more preferred. Values intermediate of those set forth herein are also intended to be within the scope of the present invention and a preferred binding affinity can be indicated as a range of affinities, for example, $10^{-6}$ to $10^{-10}$ M, preferably $10^{-7}$ to $10^{-10}$ M, more preferably $10^{-8}$ to $10^{-10}$ M. An antibody that "does not exhibit significant cross-reactivity" is one that will not appreciably bind to an undesirable entity (for example, an undesirable protein, polypeptide, or peptide). For example, an antibody that specifically binds to Aβ will appreciably bind Aβ but will not significantly react with non-Aβ proteins or peptides (for example, non-Aβ proteins or peptides included in plaques). An antibody specific for a particular epitope will, for example, not significantly cross-react with remote or different epitopes on the same protein or peptide. Specific binding can be determined according to any art-recognized means for determining such binding. Preferably, specific binding is determined according to Scatchard analysis and/or competitive binding assays.

Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, for example, Songsivilai & Lachmann, *Clin. Exp. Immunol.* 79:315-321 (1990); Kostelny et al., *J. Immunol.* 148, 1547-1553 (1992).

An "antigen" is a molecule (for example, a protein, polypeptide, peptide, carbohydrate, or small molecule) containing an antigenic determinant to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, for example, *Epitope Mapping Protocols in Methods in Molecular Biology*, Vol. 66, G. E. Morris, Ed. (1996).

In addition to the anti-Aβ antibodies described above, other Aβ binding proteins include antibody fusion proteins. The terms "antibody fusion protein" and "antibody fusion" refers to a fusion protein including all or a portion of an antibody fused to at least one non-antibody protein portion or polypeptide. Fusion is generally accomplished by genetic engineering of the gene encoding said protein. Additional exemplary antibody fusion proteins include the cell receptor binding portion of an antibody (including the Fc region) fused to all or a portion of another soluble or cellular biological protein, for example a receptor (cellular or soluble) or portion thereof, a cytokine or portion thereof, an enzyme or portion thereof, etc. In particular, an antibody fusion protein of the invention that can comprise the Fc region of an antibody fused to a non-antibody protein portion or polypeptide that is capable of binding to Aβ.

The term "Fc binding agent" refers to a molecule that is capable of binding to the Fc region of an antibody (e.g., an IgG antibody) including, but not limited to, a complement protein, an Fc receptor or a bacterial-derived protein, such as Protein A or Protein G, that has high affinity for the Fc region of an antibody.

The term "Fc region" refers to a C-terminal region of an IgG antibody, in particular, the C-terminal region of the heavy chain(s) of said IgG antibody. Although the boundaries of the Fc region of an IgG heavy chain can vary slightly, a Fc region is typically defined as spanning from about amino acid residue Cys226 to the carboxyl-terminus of an IgG heavy chain(s).

Chromatography Related Definitions

The term "source liquid", as used herein, refers to a liquid containing at least one target substance which is sought to be purified from other substances also present. Source liquids can, for example, be aqueous solutions, organic solvent systems, or aqueous/organic solvent mixtures or solutions. The source liquids are often complex mixtures or solutions containing many biological molecules (such as proteins, antibodies, hormones, and viruses), small molecules (such as salts, sugars, lipids, etc.) and even particulate matter. While a typical source liquid of biological origin may begin as an aqueous solution or suspension, it may also contain organic solvents used in earlier separation steps such as solvent precipitations, extractions, and the like. Examples of source liquids that may contain valuable biological substances amenable to the purification by various embodiments the present invention include, but are not limited to, a culture supernatant from a bioreactor, a homogenized cell suspension, plasma, plasma fractions, and milk.

The term "target substance" or "target protein" or "target antibody" refers herein to the one or more desired Aβ binding proteins, e.g., anti-Aβ antibodies, to be purified from the source liquid. The target substance may be present in the source liquid as a suspension or in solution.

The term "impurities" refers to materials in the source liquid that are different from the target substance(s) and are desirably excluded from the final target substance product(s). Typical impurities include nucleic acids, proteins (including intron-read-through species, low molecular weight species and under disulfide bonded species), peptides, endotoxins, viruses and small molecules.

The term "by-product" includes undesired products, which detract, or diminish the proportion of therapeutic protein of the invention.

The term "high molecular weight species" refers to protein complexes which have a molecular weight which is greater than the desired protein of the invention. In the case of an antibody, for example, an IgG antibody, such aggregates are greater than about 150 kD.

The term "low molecular weight species" refers to proteins, for example, degradation products, which have a molecular weight which is less than the desired protein of the invention. In the case of an antibody, for example, an IgG antibody, such degradation products are less than about 150 kD.

As used herein, the term "solid phase" refers to a non-aqueous matrix with which a target substance interacts during purification or to which an Fc binding agent can adhere. Suitable solid phase materials include, but are not limited to, glass, silica (e.g., silica gel), polysaccharides (e.g., a polysaccharide matrix) such as agarose and cellulose, organic polymers such as polyacrylamide, methylmethacrylate, and polystyrene-divinylbenzene copolymers such as for example Amberlite™ resin, (commercially available from Rohm & Haas Chemical Co., Philadelphia, Pa.). The solid phase can be selected from any of the groups of resins commonly described as affinity, ion exchange and ion capture resins. The solid phase can be, for example, a purification column, a discontinuous phase of discrete particles, or a combination thereof. The solid phase can be of porous or nonporous character, and can be compressible or incompressible. In various embodiments, the solid phase is a polymeric matrix or an agarose particle or bead. In various embodiments, the solid phase can be coated with a reagent (such as glycerol), for example, to prevent nonspecific adherence of impurities to the solid phase. An Fc binding solid phase need only possess a chemistry or an associated ligand that will permit Fc binding agent to adhere to the surface of the solid phase. Preferred solid phase materials will be physically and chemically resilient to the conditions employed in the purification process including pumping and cross-flow filtration, and temperatures, pH, and other aspects of the liquids employed.

"Affinity ligand" refers to a moiety that binds selectively or preferentially to a component of the source liquid through a specific interaction with a binding site of the component. In the present invention, the affinity ligand (e.g., an Fc binding agent) is typically immobilized to a solid phase such as a resin. Examples of affinity ligands that can be bound to the resin support to provide chromatography resins useful in the process of the present invention include, but are not limited to, Protein A, Protein G, and their analogs, which selectively bind to a protein Fc region. Methods of binding affinity ligands to solid support materials are well known in the purification art. See, e.g., the reference texts Affinity Separations: A Practical Approach (Practical Approach Series), Paul Matejtschuk (Editor), Irl Pr: 1997; and Affinity Chromatography, Herbert Schott, Marcel Dekker, New York: 1997.

"Affinity chromatography resin" or "affinity resin" refers to a chromatography resin that comprises a solid phase or substrate with affinity ligands bound to its surfaces. "Ion exchange chromatography resin" or "ion exchange resin" refers to a solid support to which are covalently bound ligands that bear a positive or negative charge, and which thus has free counterions available for exchange with ions in a solution with which the ion exchange resin is contacted.

"Cation exchange resins" refers to an ion exchange resin with covalently bound negatively charged ligands, and which thus has free cations for exchange with cations in a solution with which the resin is contacted. A wide variety of cation exchange resins are known in the art, for example, those wherein the covalently bound groups are carboxylate or sulfonate. Commercially available cation exchange resins include CMC-cellulose, SP-Sephadex™, and Fast S-Sepharose™ (the latter two being commercially available from Pharmacia).

"Anion exchange resins" refers to an ion exchange resin with covalently bound positively charged groups, such as quaternary amino groups. Commercially available anion exchange resins include DEAE cellulose, TMAE, QAE Sephadex™, and Fast Q Sepharose™ (the latter two being commercially available from Pharmacia).

As used herein, the term "chaotropic salt" refers to a salt which comprises one or more ionic components that are low in the lyotropic series that are able to penetrate protein hydration shells and bind directly to their surfaces. This disrupts cohydrative association, favoring protein solubilization. Examples of chaotropic salts include, but are not limited to, halide salts of the Group II elements (e.g., calcium chloride, magnesium chloride, barium chloride, calcium bromide, magnesium bromide, barium bromide, calcium iodide, magnesium iodide, barium iodide).

Examples of suitable divalent cations salts include, but are not limited to, salts of $Mn^{2+}$, $Ni^{2+}$ or $Cu^{2+}$, $Mg^{2+}$, $Ca^{2+}$ and $Ba^{2+}$ with thiocyanate ($SCN^-$), perchlorate ($ClO_4^-$), nitrate ($NO_3^-$), chloride ($Cl^-$), and bromide ($Br^-$); and combinations thereof.

In certain embodiments, the divalent cation salt comprises a divalent cation (e.g., $Mg^{2+}$, $Ca^{2+}$, $Ni^{2+}$ or $Ba^{2+}$). Preferred chaotropic salts for use in the featured processes are $MgCl_2$, $NiCl_2$ and $CaCl_2$. After the divalent cation salt wash step, the target protein is eluted from the affinity chromatography matrix.

A "buffer" is a substance which, by its presence in solution, increases the amount of acid or alkali that must be added to cause unit change in pH. A buffered solution resists changes in pH by the action of its acid-base conjugate components. Buffered solutions for use with biological reagents are generally capable of maintaining a constant concentration of hydrogen ions such that the pH of the solution is within a physiological range. The term "physiological pH" refers to the pH of mammalian blood (i.e., 7.38 or about 7.4). Thus a physiologic pH range is from about 7.2 to 7.6. Traditional buffer components include, but are not limited to, organic and inorganic salts, acids and bases. Exemplary buffers for use in purification of biological molecules (e.g., protein molecules) inlcude the zwitterionic or "Good" Buffers, see e.g., Good et al. (1966) *Biochemistry* 5:467 and Good and Izawa (1972) *Methods Enzymol.* 24:62. Exemplary buffers include but are not limited to TES, MES, PIPES, HEPES, MOPS, MOPSO, TRICINE and BICINE.

The "equilibration buffer" herein is a buffer used to prepare the Fc binding reagent, solid phase, or both, for loading of the source liquid containing the target protein. The equilibration buffer is preferably isotonic and commonly has a pH in the range from about 6 to about 8. The "loading buffer" is a buffer used to load the source liquid containing the Aβ binding protein, e.g, anti-Aβ antibody, and impurities onto the solid phase to which the Fc binding agent is immobilized. Often, the equilibration and loading buffers are the same. The "elution buffer" is used to elute the Aβ binding protein from the immobilized Fc binding agent. Preferably the elution buffer has a low pH and thereby disrupts interactions between the Fc binding agent and the protein of interest. Preferably, the low pH elution buffer has a pH in the range from about 2 to about 5, most preferably in the range from about 3 to about 4. Examples of buffers that will control the pH within this range include glycine, phosphate, acetate, citrate and ammonium buffers, as well as combinations of these. The preferred such buffers are citrate and acetate buffers, most preferably sodium citrate or sodium acetate buffers. Other elution buffers are contemplated including high pH buffers (e.g., those having a pH of 9 or more) or buffers comprising a compound or composition such as $MgCl_2$ (2 mM) for eluting the protein of interest.

"Wash liquid" or "wash buffer" as used herein all refer herein to the liquid used to carry away impurities from the chromatography resin to which is bound the target substance. More than one wash liquid can be employed sequentially, e.g., with the successive wash liquids having varying properties such as pH, conductivity, solvent concentration, etc., designed to dissociate and remove varying types of impurities that are non-specifically associated with the chromatography resin.

"Elution liquid" or "elution buffer" refers herein to the liquid that is used to dissociate the target substance from the chromatography resin after it has been washed with one or more wash liquids. The elution liquid acts to dissociate the target substance without denaturing it irreversibly. Typical elution liquids are well known in the chromatography art and may have higher concentrations of salts, free affinity ligands or analogs, or other substances that promote dissociation of the target substance from the chromatography resin. "Elution conditions" refers to process conditions imposed on the target substance-bound chromatography resin that dissociate the target substance from the chromatography resin, such as the contacting of the target substance-bound chromatography resin with an elution liquid or elution buffer to produce such dissociation.

"Cleaning liquid" or "cleaning buffer" refers herein to the liquid that is used to wash the chromatography resin after the completion of the purification process. The cleaning liquid may contain a detergent, a virus-inactivating agent, or relatively high concentrations of salts, and may have a higher or lower pH than the liquids used during the purification process. Its purpose is to decontaminate the chromatography resin to render it ready for reuse. Typical cleaning liquids are well-known in the chromatography art.

"Storage liquid" or "storage buffer" refers herein to the liquid in which the chromatography resin is suspended between uses. Storage liquids, in addition to buffering ions, may also contain microbicides or other preservatives. Such storage liquids are well known in the chromatography art.

In various aspects, the present invention features methods for purifying an Aβ binding protein, preferably an anti-Aβ antibody, from a source liquid comprising the protein and one or more impurities by adsorbing the protein to an Fc binding agent, followed by washing the Fc binding agent with a buffer solution containing a divalent cation salt to remove one or more impurities, and subsequently recovering the protein from the Fc binding agent. Suitable Fc binding agents include, but are not limited to, Protein A and Protein G.

The present invention features processes for the purification of Aβ binding proteins, in particular anti-Aβ antibodies. Exemplary purification processes include an affinity chromatography step. The affinity chromatography step can be continuous, discontinuous, or a combination of both. For example, the affinity chromatography step can be performed as a discontinuous process, such as, for example, a batch process. Affinity chromatography is the process of bioselective adsorption and subsequent recovery of a target compound from an immobilized ligand. This process allows for the highly specific and efficient purification of the target compound. The process requires the utilization of an appropriately selective ligand (e.g., Fc binding agent) which will bind the target compound (e.g., anti-Aβ antibody) generally with a dissociation constant in the range of $10^{-4}$ to $10^{-8}$, while permitting recovery under mild conditions. The ligand is generally immobilized on a beaded and porous matrix which may be in the form of a column packing or batchwise adsorption medium.

A preferred binding agent is Protein A. Protein A binds the Fc region of immunoglobulins. Protein A consists of six regions, five of which bind IgG. It binds with high affinity to human $IgG_1$, $IgG_2$ and $IgG_4$, as well as mouse $IgG_{2a}$, $IgG_{2b}$ and $IgG_3$. Protein A binds with moderate affinity to human IgD, IgM, IgA and IgE as well as mouse $IgG_1$. As an affinity ligand, protein A is immobilized to a matrix so that these regions are free to bind. One molecule of immobilized protein A can bind at least two molecules of IgG. Native and recombinant versions of protein A share similar specificity for the Fc region of IgG. Recombinant protein A (Protein A) can be engineered to include, for example, a C-terminal cysteine, and can be immobilized via thioetser coupling to a solid phase matrix. Such coupling results in enhanced binding capacity of the protein A.

An alternative binding agent is Protein G. Protein G is specific for IgG, binding with high affinity for human $IgG_1$, $IgG_2$, $IgG_3$ and $IgG_4$, as well as mouse $IgG_1$, and $IgG_3$. Protein G PLUS has moderate affinity for human $IgG_4$ and mouse $IgG_{2a}$, $IgG_{2b}$ and $IgG_3$. Recombinant protein G (rProteinG) can be engineered to delete the albumin-binding region of the native protein. Recombinant Protein G contains two Fc binding regions.

An alternative binding agent is Protein A/G. Protein A/G is a genetically-engineered protein that combines the IgG binding profiles of both Protein A and Protein G. It is a gene fusion product secreted from a nonpathogenic form of Bacillus. Protein A/G contains four Fc binding domains from Protein A and two from Protein G. Protein A/G is not as pH dependent as Protein A, but otherwise has the additive properties of Protein A and G.

Protein A/G binds to all human IgG subclasses, particularly suitable for purification of polyclonal or monoclonal IgG antibodies whose subclasses have not been determined. In addition, it binds to IgA, IgE, IgM and (to a lesser extent) IgD. Protein A/G also binds well to all mouse IgG subclasses, particularly suitable for purification of mouse monoclonal antibodies from IgG subclasses, without interference from IgA, IgM and murine serum albumin. (See e.g., Sikkema. (1989) *Amer. Biotech. Lab* 7, 42.) Individual subclasses of mouse monoclonals can have a stronger affinity for the chimeric Protein A/G than to either Protein A or Protein G. (See e.g., Eliasson et al. (1988) *J. Biol. Chem.* 263, 4323-4327.)

In the present invention, the immobilized Fc binding agent (e.g., Protein A) is washed with a divalent cation salt solution to remove impurities. In particular, it has been discovered that undesirable impurities produced as a result of recombinant antibody expression technologies can be removed using a divalent cation salt wash step.

The methods of the present invention can optionally include purification steps subsequent to the affinity chromatography and divalent cation wash step. Subsequent purification steps can include an ion exchange chromatography step and/or a hydrophobic interaction chromatography (HIC) step. Subsequent chromatography steps can be continuous, discontinuous (e.g., such as a batch process), or a combination of both. Ion exchange chromatography separates molecules based on differences between the overall charge of the proteins. The target protein must have a charge opposite that of the functional group attached to the resin in order to bind. For example, antibodies, which generally have an overall positive charge, will bind well to cation exchangers, which contain negatively charged functional groups. Because this interaction is ionic, binding must take place under low ionic conditions. Elution is achieved by increasing the ionic strength to break up the ionic interaction, or by changing the pH of the protein. Whereas ion exchange chromatography relies on the charges of proteins to isolate them, hydrophobic interaction chromatography uses the hydrophobic properties of some proteins. Hydrophobic groups on the protein bind to hydrophilic groups on the column. The more hydrophobic a protein is, the stronger it will bind to the column. The HIC step removes, for example, host cell derived impurities (e.g., DNA and other high and low molecular weight product-related species). Further purification steps can include virus removing steps as well as ultrafiltration and/or diafiltration steps, as described herein.

In various embodiments, the Fc region containing protein is an antibody or an antibody fuision protein having an Fc region that binds to an Fc receptor of the Fc binding agent. The use of the buffer solution containing a divalent cation salt to wash the Fc binding agent allows for greater removal of impurities, such as, for example, read-through variants and constant region containing fragments (including LMW and UDB species), of the protein of interest (e.g., the target substance in the source liquid).

The methods of the present invention comprise one or more chromatographic separation steps and in addition can comprise one or more filtration steps for separating an Aβ binding protein ("the target protein") from impurities in a source liquid.

For example, the source liquid may be filtered, centrifuged or otherwise processed to remove particulate debris and the like before contacting the source liquid with the Fc binding agent. For example, using recombinant techniques, proteins can be produced intracellularly, in the periplasmic space, or secreted directly into the culture medium. If the protein is produced intracellularly, the particulate debris, either host cells or lysed fragments, can be removed, for example, by centrifugation or ultrafiltration. Where the protein is secreted into the medium, the recombinant host cells can be separated from the cell culture medium, for example, by tangential flow filtration.

In various embodiments, the source liquid containing the target protein is contacted with an Fc binding agent (preferably immobilized on a solid phase and equilibrated with a suitable buffer) such that the target protein adsorbs to the Fc binding agent (e.g., an immobilized Fc binding agent). The source liquid is contacted with the Fc binding agent (e.g., an immobilized Fc binding agent) in a loading buffer which may be the same as the equilibration buffer. As the impurity-containing source liquid flows through the solid phase, the target protein is adsorbed to the Fc binding agent and various other impurities (such as host cell proteins, where the target protein is produced in a recombinant host cell, or other process-derived impurities) flow-through or bind nonspecifically to the solid phase. In various embodiments, the Fc binding agent is Protein A, and the equilibration buffer can be 20 mM Tris, 0.15 M NaCl, pH 7.5. Other suitable equilibration buffers include, for example, BIS, HEPES, etc., at physiological concentrations, for example, concentration in the range between about 0.5 mM and about 100 mM (e.g., 10 mM, 20 mM, 50 mM, etc.), and physiological salt concentrations (e.g., about 0.15 mM NaCl), and at pH from 5.0-9.0.

The solid phase is preferably an agarose (e.g., Sepharose) bead or particle for immobilizing the Fc binding agent. In various embodiments, the column is coated with a reagent, such as glycerol, to decrease or prevent nonspecific adherence to the column. In various embodiments, the Fc binding agent is Protein A. The rmp Protein A Sepharose™ Fast Flow (FF) column, commercially available from Amersham Biosciences, is an example of a suitable Protein A column for use in the featured methodologies.

The Fc binding agent is then washed with a buffered wash solution containing a divalent cation salt to remove protein variant species bound to the solid phase or Fc binding agent. In particular, it has been discovered that the use of a divalent cation salt wash step can remove a significant amount of undesirable impurities. Specifically, it has been discovered that in iron read-through variants, low molecular weight variants and under-disulfide bonded variants of an anti-Aβ antibody can be removed using a divalent cation salt wash. Moreover, host cell proteins (HCP) and DNA also can be removed using the divalent cation salt wash. In various embodiments, the divalent cation salt in the wash solution contains a chaotropic salt. Examples of suitable chaotropic salts include, but are not limited to, calcium chloride ($CaCl_2$), nickel chloride ($NiCl_2$) and magnesium chloride ($MgCl_2$). While a single divalent cation salt can be present in the wash solution, in various embodiments, two or more divalent cation salts can be used.

In various embodiments, wash solutions in addition to the divalent cation salt containing wash solution are used to remove impurities. For example, in various embodiments a 20 to 50 mM Tris, 0.75 to 2.0 M NaCl, pH 5.0-9.0 solution, and/or a 10 mM Tris, pH 7.5 solution are used to wash the Fc binding agent prior to, after, or both prior to and after, washing Fc binding agent with the divalent cation salt containing wash solution.

In various embodiments, the divalent cation salt is preferably added at a concentration between about 0.5 M and about 2.5 M to a pH buffered solution having a pH in the range from about 5 to about 9, and preferably a pH in the range from about 7 to about 8. Preferred concentrations of the divalent cation salt include, but are not limited to, 0.6 M, 2.0 M and 2.5 M. Suitable buffers for this purpose include, but are not limited to, Tris or acetate buffers in a concentration from 20 to 50 mM.

Following the washing step(s), the target protein is recovered from the Fc binding agent. This is normally achieved using a suitable elution buffer. The target protein can, for example, be eluted from the column using an elution buffer having a low pH, e.g., in the range from about 2 to about 6.5, and preferably in the range from about 2.5 to about 3.5.

In various embodiments, the target protein thus recovered can be formulated in a pharmaceutically acceptable carrier and used for various diagnostic, therapeutic or other uses known for such molecules.

In various embodiments, the eluted target protein preparation can be subjected to additional purification steps after the Fc binding agent chromatography step. For example, exemplary further purification steps include, but are not limited to: anion exchange chromatography, cation exchange chromatography, hydrophobic interaction chromatography (HIC), hydroxyapatite chromatography, dialysis, affinity chromatography (including immobilized metal affinity chromatography), size exclusion chromatography (SEC), ammonium sulphate precipitation, ethanol precipitation, reverse phase HPLC (RP-HPLC), chromatofocusing, ultrafiltration, diafiltration, and gel filtration. In various embodiments, the Fc binding agent chromatography step is followed by an anion exchange chromatography and a HIC step. In various embodiments, the chromatography steps are further followed by a virus filtration step, an ultrafiltration/diafiltration step, and a microbial contaminant filtration step. In various embodiments, these additional purification steps may be conducted prior to the Fc binding agent chromatography step.

In various embodiments, methods for purification of an Aβ binding protein, preferably an anti-Aβ antibody, begin with adsorbing the target protein to an Fc binding agent comprising Protein A immobilized on a solid phase, followed by washing the Fc binding agent with a buffer solution containing a divalent cation salt to remove one or more impurities, and subsequently recovering the protein from the Protein A to produce a first eluent pool.

In various embodiments, the purification process continues with subjecting the first eluent pool to anion exchange chromatography by contacting an anion exchange resin with the first eluent pool such that impurities adsorb to the resin, while the target protein does not adsorb to the resin. Thus, the target protein can be recovered from the flow-through to produce a second eluent pool. In various embodiments, the anion exchange chromatography step further comprises washing the anion exchange resin with a buffered wash solution to recover at least a portion of the adsorbed target protein, which would then be combined with the second eluent pool. Alternatively, the first eluent pool may be contacted with the anion exchange resin in such a way that the antibody adsorbs, allowing any impurities to flow-through, optionally followed by washing and eluting the adsorbed antibody.

In various embodiments, the purification process continues with subjecting the second eluent pool to HIC by adsorbing the target protein to a hydrophobic interaction resin (e.g., a solid phase functionalized with hydrophobic ligands), washing the hydrophobic interaction resin with a buffered wash solution with an ionic strength which does not substantially elute the target protein, and recovering the target protein (typically using an elution buffer with an ionic strength low enough to desorb the target protein from the hydrophobic interaction resin) on a third eluent pool. Alternatively, the second eluent pool may be contacted with the HIC column in such a way that the target protein does not adsorb, recovering the flow-through target protein as a third eluent pool.

In various embodiments, the purification process includes one or more filtration steps, for example, to remove viruses, concentrate and buffer the solution containing the target protein, and to remove microbial contaminants.

In various embodiments, the present invention provides methods for the purification of an Aβ binding protein, preferably an anti-Aβ antibody, from a source liquid comprising the protein and one or more impurities where the impurities comprise one or more IRT variants. In one embodiment, the methods provide for about a 2 to about a 20 fold reduction in IRT variant levels from those in the source liquid. Preferably, IRT variant levels are reduced by at least 5 fold, and more preferably IRT variant levels are reduced by at least 10 fold. For example, in a source liquid (starting sample) having about 3-5% IRT antibody variants (as a percentage of total species in the source liquid) IRT antibody variant species can be reduced to about 0.3 to about 0.5%. In various embodiments, IRT variant species are reduced to: less than 1%, less than 0.8%, less than 0.5%, less than 0.3%, less than 0.2%, and/or less than 0.1%. Preferably, in the purification of a source liquid for the preparation of a protein, IRT variants are reduced to: less than 1%, less than 0.8%, less than 0.5%, less than 0.3%, less than 0.2%, and/or less than 0.1% as a percentage of total species in the source liquid.

In various embodiments, the present invention provides methods for the purification of an Aβ binding protein, preferably an anti-Aβ antibody, from a source liquid comprising the protein and one or more impurities where the impurities comprise one or more LMW variants. In one embodiment, the methods provide for about a 2 to about a 20 fold reduction in LMW variant levels from those in the source liquid. Preferably, LMW variant levels are reduced by at least 5 fold, and more preferably LMW variant levels are reduced by at least 10 fold. For example, in a source liquid (starting sample) having about 3-5% LMW antibody variants (as a percentage of total species in the source liquid) LMW antibody variant species can be reduced to about 0.3 to about 0.5%. In various embodiments, LMW variant species are reduced to: less than 1%, less than 0.8%, less than 0.5%, less than 0.3%, less than 0.2%, and/or less than 0.1%. Preferably, in the purification of a source liquid for the preparation of a protein, LMW variants are reduced to: less than 1%, less than 0.8%, less than 0.5%, less than 0.3%, less than 0.2%, and/or less than 0.1% as a percentage of total species in the source liquid.

In various embodiments, the present invention provides methods for the purification of an Aβ binding protein, preferably an anti-Aβ antibody, from a source liquid comprising the protein and one or more impurities where the impurities comprise one or more UDB variants. In one embodiment, the methods provide for about a 2 to about a 20 fold reduction in UDB variant levels from those in the source liquid. Preferably, UDB variant levels are reduced by at least 5 fold, and more preferably UDB variant levels are reduced by at least 10 fold.

For example, in a source liquid (starting sample) having about 20% UDB antibody variants (as a percentage of total species in the source liquid) UDB antibody variant species can be reduced to about 10% to about 2%. In various embodiments, UDB variant species are reduced to: less than 20%, less than 15%, less than 10%, less than 5%, less than 2%, or less than 1%. Preferably, in the purification of a source liquid for the preparation of a protein, UDB variants are reduced to: less than 20%, less than 15%, less than 10%, less than 5%, less than 2%, or less than 1% as a percentage of total species in the source liquid.

Also, for example, in a source liquid (starting sample) having about 3-5% UDB antibody variants (as a percentage of total species in the source liquid) UDB antibody variant species can be reduced to about 0.3 to about 0.5%. In various embodiments, UDB variant species are reduced to: less than 1%, less than 0.8%, less than 0.5%, less than 0.3%, less than 0.2%, and/or less than 0.1%. Preferably, in the purification of a source liquid for the preparation of a protein, UDB variants are reduced to: less than 1%, less than 0.8%, less than 0.5%, less than 0.3%, less than 0.2%, and/or less than 0.1% as a percentage of total species in the source liquid.

Aβ Binding Proteins for use in the Purification Methods of the Invention

The Aβ binding proteins, e.g, anti-Aβ antibodies, to be purified according to the invention as described herein, can be prepared using techniques which are well established in the art and include, for example, synthetic techniques (such as recombinant techniques and peptide synthesis or a combination of these techniques), or may be isolated from an endogenous source of the protein. In various embodiments, the antibody can be, for example, a polyclonal antibody preparation, a monoclonal antibody, a recombinant antibody, a chimeric antibody, a humanized antibody or a human antibody. Techniques for the production of antibodies are described further below. In other embodiments, the Aβ binding protein can be an antibody fusion protein that comprises an antibody Fc region fused to a portion of a protein or polypeptide that is capalble of binding to Aβ. Preparation of antibody fusion proteins is also described further below.

Polyclonal Antibodies

Polyclonal antibodies can be prepared by immunizing a suitable subject with an immunogen. The antibody titer in the immunized subject can be monitored over time by standard techniques, such as with an enzyme linked immunosorbent assay (ELISA) using immobilized target antigen. If desired, the antibody molecules directed against the target antigen can be isolated from the mammal (for example, from the blood) and further purified by well known techniques, such as protein A Sepharose chromatography to obtain the antibody, for example, IgG, fraction. At an appropriate time after immunization, for example, when the anti-antigen antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75). For the preparation of chimeric polyclonal antibodies, see Buechler et al. U.S. Pat. No. 6,420,113.

Monoclonal Antibodies

Any of the many well known protocols used for fusing lymphocytes and immortalized cell lines can be applied for the purpose of generating a monoclonal antibody (see, for example, G. Galfre et al. (1977) *Nature* 266:55052; Gefter et al. *Somatic Cell Genet.*, cited supra; Lerner, *Yale J Biol. Med.*, cited supra; Kenneth, *Monoclonal Antibodies*, cited supra). Moreover, the ordinarily skilled worker will appreciate that there are many variations of such methods which also would be useful. Typically, the immortal cell line (for example, a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, for example, the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a target antigen using a standard ELISA assay.

Recombinant Antibodies

Alternative to preparing monoclonal antibody-secreting hybridomas, a monoclonal antibody can be identified and isolated by screening a recombinant combinatorial immunoglobulin library (for example, an antibody phage display library) with a target antigen to thereby isolate immunoglobulin library members that bind the target antigen. Kits for generating and screening phage display libraries are commercially available (for example, the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et aL PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991)

*Proc. Natl. Acad. Sci. USA* 88:7978-7982; and McCafferty et al. *Nature* (1990) 348:552-554.

Chimeric and Humanized Antibodies

Additionally, recombinant antibodies, such as chimeric and humanized monoclonal antibodies, comprising both human and non-human portions, which can be made using standard recombinant DNA techniques, are within the scope of the invention.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (for example, at least one CDR, preferably two CDRs, more preferably three CDRs) substantially from a non-human immunoglobulin or antibody, and further includes constant regions (for example, at least one constant region or portion thereof, in the case of a light chain, and three constant regions in the case of a heavy chain). The term "humanized variable region" (for example, "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90%, 90-95%, or 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably at least 90-95%, more preferably, 96%, 97%, 98%, or 99% identical to that of a non-human organism, for example, a non-human mammal.

Accordingly, all regions or residues of a humanized immunoglobulin or antibody, or of a humanized immunoglobulin or antibody chain, except the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The term "significant identity" means that two polypeptide sequences, when optimally aligned, such as by the programs GAP or BESTFIT using default gap weights, share at least 50-60% sequence identity, preferably at least 60-70% sequence identity, more preferably at least 70-80% sequence identity, more preferably at least 80-90% sequence identity, even more preferably at least 90-95% sequence identity, and even more preferably at least 95% sequence identity or more (for example, 99% sequence identity or more). The term "substantial identity" means that two polypeptide; sequences, when optimally aligned, such as by the programs GAP or BESTFIT using default gap weights, share at least 80-90% sequence identity, preferably at least 90-95% sequence identity, and more preferably at least 95% sequence identity or more (for example, 99% sequence identity or more). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Preferably, residue positions which are not identical differ by conservative amino acid substitutions. For purposes of classifying amino acids substitutions as conservative or non-conservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI, (aromatic side chains): trp, tyr, phe. Conservative substitutions involve substitutions between amino acids in the same class. Non-conservative substitutions constitute exchanging a member of one of these classes for a member of another.

Preferably, humanized immunoglobulins or antibodies bind antigen with an affinity that is within a factor of three, four, or five of that of the corresponding non-humanized antibody. For example, if the nonhumanized antibody has a binding affinity of $10^{-9}$ M, humanized antibodies will have a binding affinity of at least $3\times10^{-8}$ M, $4\times10^{-8}$ M, $5\times10^{-8}$ M, or $10^{-9}$ M. A immunoglobulin chain is said to "direct antigen binding" when it confers upon an intact immunoglobulin or antibody (or antigen binding fragment thereof) a specific binding property or binding affinity. A mutation (for example, a backmutation) is said to substantially affect the ability of a heavy or light chain to direct antigen binding if it affects (for example, decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (for example, decrease) the ability of a chain to direct antigen binding" if it affects (for example, decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application. 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et aL (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225, 539; Jones et al. (1986) *Nature* 321:552-525; Verhoeyan et al. (1988) *Science* 239:1534; and Beidler et al. (1988) *J. Immunol.* 141:4053-4060.

Human Antibodies from Transgenic Animals and Phase Display

Alternatively, it is now possible to produce transgenic animals (for example, mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice results in the production of human antibodies upon antigen challenge. See, for example, U.S. Pat. Nos. 6,150,584; 6,114,598; and 5,770,429.

Fully human antibodies can also be derived from phage-display libraries (Hoogenboom et al., J. Mol. Biol., 227:381 (1991); Marks et al., J. Mol. Biol., 222:581-597 (1991)). Chimeric polyclonal antibodies can also be obtained from phage display libraries (Buechler et al. U.S. Pat. No. 6,420, 113).

Bispecific Antibodies and Antibody Conjugates

Bispecific antibodies (BsAbs) are antibodies that have binding specificities for at least two different epitopes. Such antibodies can be derived from full length antibodies or antibody fragments (for example F(ab)'2 bispecific: antibodies). Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of different antibody molecules (see, WO 93/08829 and in Traunecker et al., EMBO J., 10:3655-3659 (1991)).

Bispecific antibodies also include cross-linked or "heteroconjugate" antibodies. For example, one of the antibodies in the heteroconjugate can be coupled to avidin, the other to biotin or other payload. Heteroconjugate antibodies may be made using any convenient cross-linking methods. Suitable cross-linking agents are well known in the art, and are disclosed in U.S. Pat. No. 4,676,980, along with a number of cross-linking techniques.

In yet another embodiment, the antibody can be conjugated, chemically or genetically, to a payload such as a reactive, detectable, or functional moiety, for example, an immunotoxin to produce an antibody conjugate. Such payloads include, for example, immunotoxins, chemotherapeutics, and radioisotopes, all of which are well-known in the art.

Antibody Fusion Proteins

An Aβ binding protein having an Fc region as used in the invention can be a fusion protein that contains at least the Fc portion of an antibody fused to a non-antibody protein or polypeptide that is capable of binding Aβ. Thus, a soluble fusion protein is created that is capable of binding Aβ and that has Fc-related functions (such as serum stability, Fc receptor binding and the like). Antibody fusion proteins (also referred to in the art as Fc fusion proteins or Ig fusion proteins) can be prepared using standard recombinant DNA techniques and have been described in the art, see for example U.S. Pat. No. 5,116,964, U.S. Pat. No. 5,225,538, U.S. Pat. No. 5,336,603 and U.S. Pat. No. 5,428,130, all by Capon et al.

Anti Aβ Antibodies

Generally, the antibodies of the present invention include a variety of antibodies for treating amyloidogenic diseases, in particular, Alzheimer's Disease, by targeting Aβ peptide.

The terms "Aβ antibody", "anti Aβ antibody" and "anti Aβ" are used interchangeably herein to refer to an antibody that binds to one or more epitopes or antigenic determinants of the human amyloid precursor protein (APP), Aβ protein, or both. Exemplary epitopes or antigenic determinants can be found within APP, but are preferably found within the Aβ peptide of APP. Multiple isoforms of APP exist, for example $APP^{695}$, $APP^{751}$ and $APP^{770}$. Amino acids within APP are assigned numbers according to the sequence of the $APP^{770}$ isoform (see for example, GenBank Accession No. P05067). Examples of specific isotypes of APP which are currently known to exist in humans are the 695 amino acid polypeptide described by Kang et. al. (1987) *Nature* 325:733-736 which is designated as the "normal" APP; the 751 amino acid polypeptide described by Ponte et al. (1988) *Nature* 331:525-527

(1988) and Tanzi et al. (1988) *Nature* 331:528-530; and the 770-amino acid polypeptide described by Kitaguchi et. al. (1988) *Nature* 331:530-532. As a result of proteolytic processing of APP by different secretase enzymes in vivo or in situ, Aβ is found in both a "short form", 40 amino acids in length, and a "long form", ranging from 42-43 amino acids in length. The short form, Aβ$_{40}$, consists of residues 672-711 of APP. The long form, for example, Aβ$_{42}$ or Aβ$_{43}$, consists of residues 672-713 or 672-714, respectively. Part of the hydrophobic domain of APP is found at the carboxy end of Aβ, and may account for the ability of Aβ to aggregate, particularly in the case of the long form. Aβ peptide can be found in, or purified from, the body fluids of humans and other mammals, for example cerebrospinal fluid, including both normal individuals and individuals suffering from amyloidogenic disorders.

The terms "β-amyloid protein", "β-amyloid peptide", "β-amyloid", "Aβ" and "Aβ peptide" are used interchangeably herein. Aβ peptide (for example, Aβ39, Aβ40, Aβ41, Aβ42 and Aβ43) is a ~4-kDa internal fragment of 39-43 amino acids of APP. Aβ40, for example, consists of residues 672-711 of APP and Aβ42 consists of residues 672-713 of APP. Aβ peptides include peptides resulting from secretase cleavage of APP and synthetic peptides having the same or essentially the same sequence as the cleavage products. Aβ peptides can be derived from a variety of sources, for example, tissues, cell lines, or body fluids (for example sera or cerebrospinal fluid). For example, an Aβ can be derived from APP-expressing cells such as Chinese hamster ovary (CHO) cells stably transfected with APP$_{717V \rightarrow F}$, as described, for example, in Walsh et al., (2002), *Nature,* 416, pp 535-539. An Aβ preparation can be derived from tissue sources using methods previously described (see, for example, Johnson-Wood et al., (1997), *Proc. Natl. Acad. Sci. USA* 94:1550). Alternatively, Aβ peptides can be synthesized using methods which are well known to those in the art. See, for example, Fields et al., Synthetic Peptides: A User's Guide, ed. Grant, W.H. Freeman & Co., New York, N.Y., 1992, p 77). Hence, peptides can be synthesized using the automated Merrifield techniques of solid phase synthesis with the α-amino group protected by either t-Boc or F-moc chemistry using side chain protected amino acids on, for example, an Applied Biosystems Peptide Synthesizer Model 430A or 431. Longer peptide antigens can be synthesized using well known recombinant DNA techniques. For example, a polynucleotide encoding the peptide or fusion peptide can be synthesized or molecularly cloned and inserted in a suitable expression vector for the transfection and heterologous expression by a suitable host cell. Aβ peptide also refers to related Aβ sequences that results from mutations in the Aβ region of the normal gene.

Exemplary epitopes or antigenic determinants to which an Aβ antibody binds can be found within the human amyloid precursor protein (APP), but are preferably found within the Aβ peptide of APP. Exemplary epitopes or antigenic determinants within Aβ are located within the N-terminus, central region, or C-terminus of Aβ. An "N-terminal epitope", is an epitope or antigenic determinant located within or including the N-terminus of the Aβ peptide. Exemplary N-terminal epitopes include residues within amino acids 1-10 or 1-12 of Aβ, preferably from residues 1-3, 1-4, 1-5, 1-6, 1-7, 2-6, 2-7, 3-6, or 3-7 of Aβ42. Other exemplary N-terminal epitopes start at residues 1-3 and end at residues 7-11 of Aβ. Additional exemplary N-terminal epitopes include residues 2-4, 5, 6, 7 or 8 of Aβ, residues 3-5, 6, 7, 8 or 9 of Aβ, or residues 4-7, 8, 9 or 10 of Aβ42. "Central epitopes" are epitopes or antigenic determinants comprising residues located within the central or mid-portion of the Aβ peptide. Exemplary central epitopes include residues within amino acids 13-28 of Aβ, preferably from residues 14-27, 15-26, 16-25, 17-24, 18-23, or 19-22 of Aβ. Other exemplary central epitopes include residues within amino acids 16-24, 16-23, 16-22, 16-21, 18-21, 19-21, 19-22, 19-23, or 19-24 of Aβ. "C-terminal" epitopes or antigenic determinants are located within or including the C-terminus of the Aβ peptide and include residues within amino acids 33-40, 33-41, or 33-42 of Aβ. "C-terminal epitopes" are epitopes or antigenic determinants comprising residues located within the C-terminus of the Aβ peptide (for example, within about amino acids 30-40 or 30-42 of Aβ. Additional exemplary C-terminal epitopes or antigenic determinants include residues 33-40 or 33-42 of Aβ.

When an antibody is said to bind to an epitope within specified residues, such as Aβ 3-7, what is meant is that the antibody specifically binds to a polypeptide containing the specified residues (i.e., Aβ 3-7 in this an example). Such an antibody does not necessarily contact every residue within Aβ 3-7. Nor does every single amino acid substitution or deletion within Aβ 3-7 necessarily significantly affect binding affinity. In various embodiments, an Aβ antibody is end-specific. As used herein, the term "end-specific" refers to an antibody which specifically binds to the N-terminal or C-terminal residues of an Aβ peptide but that does not recognize the same residues when present in a longer Aβ species comprising the residues or in APP. In various embodiments, an Aβ antibody is "C-terminus-specific." As used herein, the term "C terminus-specific" means that the antibody specifically recognizes a free C-terminus of an Aβ peptide. Examples of C terminus-specific Aβ antibodies include those that: recognize an Aβ peptide ending at residue 40 but do not recognize an Aβ peptide ending at residue 41, 42, and/or 43; recognize an Aβ peptide ending at residue 42 but do not recognize an Aβ peptide ending at residue 40, 41, and/or 43; etc.

In one embodiment, the Aβ antibody may be a 3D6 antibody or variant thereof, or a 10D5 antibody or variant thereof, both of which are described in U.S. Patent Publication No. 20030165496A1, U.S. Patent Publication No. 20040087777A1, International Patent Publication No. WO02/46237A3 and International Patent Publication No. WO04/080419A2. Description of 3D6 and 10D5 antibodies can also be found, for example, in International Patent Publication No. WO02/088306A2 and International Patent Publication No. WO02/088307A2. Additional 3D6 antibodies are described in U.S. patent application Ser. No. 11/303,478 and International Application No. PCT/US05/45614. 3D6 is a monoclonal antibody (mAb) that specifically binds to an N-terminal epitope located in the human β-amyloid peptide, specifically, residues 1-5. By comparison, 10D5 is a mAb that specifically binds to an N-terminal epitope located in the human β-amyloid peptide, specifically, residues 3-6. A cell line producing the 3D6 monoclonal antibody (RB96 3D6.32.2.4) was deposited with the American Type Culture Collection (ATCC), Manassas, Va. 20108, USA on Apr. 8, 2003 under the terms of the Budapest Treaty and has deposit number PTA-5130. A cell line producing the 10D5 monoclonal antibody (RB44 10D5.19.21) was deposited with the ATCC on Apr. 8, 2003 under the terms of the Budapest Treaty and has deposit number PTA-5129.

Exemplary variant 3D6 antibodies are those having, for example, a humanized light chain comprising variable region amino acid sequences set forth as SEQ ID NO:3 or SEQ ID NO:5 and a humanized heavy chain comprising variable region amino acid sequences set forth as SEQ ID NO:4 or SEQ ID NO:6. Other exemplary variant 3D6 antibodies are those having, for example, a humanized light chain amino acid sequence set forth as SEQ ID NO:7 and a humanized heavy chain amino acid sequence set forth as SEQ ID NO:8.

Exemplary variant 10D5 antibodies are those having, for example, a humanized light chain comprising variable region amino acid sequences set forth as SEQ ID NO:9 or SEQ ID NO:11 and a humanized heavy chain comprising variable region amino acid sequences set forth as SEQ ID NO:10 or SEQ ID NO:12. Other exemplary variant 10D5 antibodies are those having, for example, a humanized light chain amino acid sequence set forth as SEQ ID NO:13 and a humanized heavy chain amino acid sequence set forth as SEQ ID NO:14. Such variant antibodies are further described in WO02/088307A2.

In another embodiment, the antibody may be a 12B4 antibody or variant thereof, as described in U.S. Patent Publication No. 20040082762A1 and International Patent Publication No. WO03/077858A2. 12B4 is a mAb that specifically binds to an N-terminal epitope located in the human β-amyloid peptide, specifically, residues 3-7.

Exemplary variant 12B4 antibodies are those having, for example, a humanized light chain (or light chain) comprising variable region amino acid sequences set forth as SEQ ID NO:15 or SEQ ID NO:17 and a humanized heavy chain comprising variable region amino acid sequences set forth as SEQ ID NO:16, SEQ ID NO:18 or SEQ ID NO:19.

In yet another embodiment, the antibody may be a 12A11 antibody or a variant thereof, as described in U.S. Patent Publication No. 20050118651A1, U.S. patent application Ser. No. 11/303,478, International Patent Publication No. WO04/108895A2, and International Patent Application Serial No. PCT/US05/45614. 12A11 is a mAb that specifically binds to an N-terminal epitope located in the human β-amyloid peptide, specifically, residues 3-7. A cell line producing the 12A11 monoclonal antibody was deposited with the ATCC on Dec. 13, 2005 under the terms of the Budapest Treaty and has deposit number PTA-7271.

Exemplary variant 12A11 antibodies are those having, for example, a humanized light chain comprising the variable region amino acid sequence set forth as SEQ ID NO:20 and a humanized heavy chain comprising variable region amino acid sequences set forth as SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41.

In yet another embodiment, the antibody may be a 6C6 antibody, or a variant thereof, as described in U.S. patent application Ser. No. 11/305,899 and International Application No. PCT/US05/45860. 6C6 is a mAb that specifically binds to an N-terminal epitope located in the human β-amyloid peptide, specifically, residues 3-7. A cell line producing the antibody 6C6 was deposited on Nov. 1, 2005, with the ATCC under the terms of the Budapest Treaty and assigned accession number PTA-7200.

In yet another embodiment, the antibody may be a 2H3 antibody as described in U.S. patent application Ser. No. 11/305,899 and International Application No. PCT/US05/45860. 2H3 is a mAb that specifically binds to an N-terminal epitope located in the human β-amyloid peptide, specifically, residues 2-7.

In yet another embodiment, the antibody may be a 3A3 antibody as described in U.S. patent application Ser. No. 11/305,899 and International Application No. PCT/US05/45860. 3A3 is a mAb that specifically binds to an N-terminal epitope located in the human β-amyloid peptide, specifically, residues 3-7.

Cell lines producing the antibodies 2H3 and 3A3, having the ATCC accession numbers PTA-7267 and PTA-7269 respectively, were deposited on Dec. 13, 2005 under the terms of the Budapest Treaty.

In yet another embodiment, the antibody may be a 15C11 antibody or variant thereof, as described in a U.S. patent application Ser. No. 11/304,986 and International Patent Application No. PCT/US05/45515 entitled "Humanized Antibodies that Recognize Beta Amyloid Peptide."15C11 is a mAb that specifically binds to a central epitope located in the human β-amyloid peptide, specifically, residues 19-22. A cell line producing the 15C11 monoclonal antibody was deposited with the ATCC on Dec. 13, 2005 under the terms of the Budapest Treaty and has deposit number PTA-7270.

In yet another embodiment, the antibody may be a 266 antibody as described in U.S. Patent Publication No. 20050249725A1, and International Patent Publication No. WO01/62801A2. 266 is a mAb that specifically binds to a central epitope located in the human β-amyloid peptide, specifically, residues 16-24. A cell line producing the 266 monoclonal antibody was deposited with the ATCC on Jul. 20, 2004 under the terms of the Budapest Treaty and has deposit number PTA-6123.

Exemplary variant 266 antibodies are those having, for example, a humanized light chain comprising variable region amino acid sequences set forth as SEQ ID NO:42 or SEQ ID NO:44 and a humanized heavy chain comprising variable region amino acid sequences set forth as SEQ ID NO:43 or SEQ ID NO:45. Other exemplary variant 266 antibodies are those having, for example, a humanized light chain amino acid sequence set forth as SEQ ID NO:46 and a humanized heavy chain amino acid sequence set forth as SEQ ID NO:47. Such variant antibodies are further described in U.S. Patent Publication No. 20050249725A1, and International Patent Publication No. WO01/62801A2.

In yet another embodiment, the antibody may be a 2B1 antibody, or a variant thereof, as described in a U.S. patent application Ser. No. 11/305,899 and International Patent Application No. PCT/US05/45860 entitled "β Antibodies for Use in Improving Cognition". 2B1 is a mAb that specifically binds to a central epitope located in the human β-amyloid peptide, specifically, residues 19-23.

In yet another embodiment, the antibody may be a 1C2 antibody, or a variant thereof, as described in a U.S. patent application Ser. No. 11/305,899 and International Patent Application No. PCT/US05/45860 entitled "Aβ Antibodies for Use in Improving Cognition". 1C2 is a mAb that specifically binds to a central epitope located in the human β-amyloid peptide, specifically, residues 16-23.

In yet another embodiment, the antibody may be a 9G8 antibody, or a variant thereof, as described in U.S. patent application Ser. No. 11/304,986 and International Patent Application No. PCT/US05/45515. 9G8 is a mAb that specifically binds to a central epitope located in the human β-amyloid peptide, specifically, residues 16-21.

Cell lines producing the antibodies 2B1, 1C2 and 9G8 were deposited on Nov. 1, 2005, with the ATCC under the terms of the Budapest Treaty and were assigned accession numbers PTA-7202, PTA-7199 and PTA-7201, respectively.

Antibodies that specifically bind to. C-terminal epitopes located in human β-amyloid peptide, for use in the present invention include, but are not limited to, 369.2B, as described in U.S. Pat. No. 5,786,180, entitled "Monoclonal antibody 369.2B specific for β A4 peptide." Further description of antibodies for use in the present invention can be found in, for example, Bussiere et al., (Am. J. Pathol. 165(3):987-95 (2004)) Bard et al. (PNAS 100(4):2023-8 (2003)), Kajkowski et al. (J. Biol. Chem. 276(22):18748-56 (2001)), Games et al. (Ann. NY Acad. Sci. 920:274-84 (2000)), Bard et al. (Nat. Med. 6(8):916-9 (2000)), and in International Patent Application No. WO03015691A2 entitled "Effecting rapid improvement of cognition in a subject having Alzheimer's disease, Down's syndrome, cerebral amyloid angiopathy, or mild cognitive impairment, comprises administering anti-A beta antibody". Further description of antibody fragments for use in the present invention can be found in, for example, Bales et al. (Abstract P4-396, page S587, presented at Poster Session P4: Therapeutics and Therapeutic Strategies-Therapeutic Strategies, Amyloid-Based) and Zameer et al. (Abstract P4-420, page S593, presented at Poster Session P4: Therapeutics and Therapeutic Strategies-Therapeutic Strategies, Amyloid-Based).

Antibodies for use in the present invention may be recombinantly or synthetically produced. For example, the antibody may be produced by a recombinant cell culture process, using, for example, CHO cells, NIH 3T3 cells, PER.C6® cells, NS0 cells, VERO cells, chick embryo fibroblasts, or BHK cells. In addition, antibodies with minor modifications that retain the primary functional property of binding Aβ peptide are contemplated by the present invention. In a particular embodiment, the antibody is a humanized anti Aβ peptide 3D6 antibody that selectively binds Aβ peptide. More specifically, the humanized anti Aβ peptide 3D6 antibody is designed to specifically bind to an $NH_2$-terminal epitope, for example, amino acid residues 1-5, located in the human β-amyloid 1-40 or 1-42 peptide found in plaque deposits in the brain (for example, in patients suffering from Alzheimer's disease).

An exemplary humanized anti Aβ peptide antibody is humanized 3D6 version 2 (h3D6v2). The complete amino acid sequences of the h3D6v2 light and heavy chains predicted from the DNA sequences of the corresponding expression vectors are shown in FIG. 1 (where the residues are numbered starting with the $NH_2$-terminus of light and heavy chains as residue number 1) and in SEQ ID, NO: 1 and SEQ ID NO:2, respectively. The last amino acid residue encoded by the heavy chain DNA sequence, $Lys^{449}$, has not been observed in the mature, secreted form of h3D6v2 and, without wishing to be bound to any particular theory, is presumably removed during intracellular processing by CHO cellular proteases. Therefore, the COOH-terminus of the h3D6v2 heavy chain is optionally $Gly^{448}$. COOH-terminal lysine processing has been observed in recombinant and plasma-derived antibodies and does not appear to impact their function (Harris (1995) *J. Chromatogr. A.* 705:129-134). Purified h3D6v2 is post-translationally modified by addition of N-linked glycans to the Fc portion of heavy chain, which is known to contain a single N-glycosylation consensus site. The N-glycosylation site displays three major complex biantennary neutral oligosaccharide structures commonly observed at the analogous N-glycosylation site of mammalian IgG proteins.

Another exemplary humanized anti Aβ peptide antibody is humanized 3D6 version 1 (hu3D6v1) having the sequence set forth in FIG. 1 but for a D→Y substitution at position 1 of the light chain, a S→A substitution at position 75 of the heavy chain (position 74 by Kabat numbering), a T→S substitution at position 78 of the heavy chain (position 77 by Kabat numbering), and a V→L substitution at position 93 of the heavy chain (position 89 by Kabat numbering), Various aspects and embodiments of the present invention are further described by way of the following Examples. The Examples are offered by way of illustration and not by way of limitation.

EXAMPLES

The following examples are offered for illustrative purposes only. Examples are provided using two different anti-Aβ monoclonal antibodies. Six separate experiments are described each representing a combination of antibody and impurity removal.

Materials and Methods

In general, the practice of the present invention employs, unless otherwise indicated, conventional techniques of chemistry, molecular biology, recombinant DNA technology, immunology (especially, e.g., immunoglobulin technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); Current Protocols in Molecular Biology, eds. Ausubel et al., John Wiley & Sons (1992). Bousse et al., Protein Sizing on a Microchip, *Anal. Chem.* 73, 1207-1212 (2001); Knapp et al., Commercialized and Emerging Lab-on-a-Chip Applications; In: *Proceedings of the µTAS* 2001 *Symposium*, Ramsey, J. M. & van den Berg, A., 7-10 (2001); and Mhatre et al., Strategies for locating disulfide bonds in a monoclonal antibody via mass spectrometry, *Rapid Commun. Mass Spectrom*, 13 (24) 2503-2510 (1999).

Production of Target Antibody

The target antibody can be produced, e.g., using a recombinant mammalian cell line grown in suspension culture. Conditioned medium containing the antibody of interest is generated in a production bioreactor. The resulting product may be harvested and clarified with any appropriate clarification step such as, for example, either microfiltration and 0.22 µm filtration or centrifugation, or pad filtration and 0.22 µm filtration.

Purification of Target Antibody

The purification of the target monoclonal antibodies exemplified herein AAB or 12A11) consists of capture of the target molecule on protein A affinity chromatography. This can consist of rmp Protein A Sepharose™ Fast Flow, Protein A Sepharose™ Fast Flow, or MabSelect Protein A. The resin is then washed as described for each of the experiments and the product eluted and tested for impurity levels.

Analysis of Target Antibody

Reversed-Phase HPLC (RP-HPLC) was used to quantitate the amount of IRT present in the AB monoclonal antibody samples. Size Exclusion Chromatography (SEC-HPLC) was used to determine the percentage of monomeric protein (monomeric IgG), high molecular weight (HMW), and low molecular weight (LMW) species. Denaturing SEC-HPLC analysis was carried out to determine the relative amount of Under-Disulfide Bonded (UDB) species in samples. The levels of HCP in the test samples were determined using an Enzyme-Linked immunosorbant assay (ELISA).

Analytical Assays: IRT & UDB

Reversed-Phase HPLC (AB IRTAnalysis)

The RP-HPLC was conducted as follows. Disulfide reduction of each sample was performed by incubation at 40° C. for 60 min in the presence of 2.5 mM DTT. Alkylation was performed by incubation at room temperature in the presence of 5.5 mM iodoacetic acid. Following reduction and alkylation, all samples were quenched with 5 μl of 1 M DTT. The limit of quantification for this assay is 0.5%. Approximately 40 μg of each reduced, alkylated sample was injected onto a POROS R1/H RP-HPLC column and run for 70 min under the following conditions:

Column: Poros R1/H RP-HPLC
Column Temp: 50° C.;
Mobile Phase A: 0.1% TFA (w/v) in water;
Mobile Phase B: 0.1% TFA (w/v) in 95% acetonitrile;
Flow rate: 1.0 mL/min
Detection: 217 nm
Run Time: 70 minutes
Injection: Triplicate of 40 μg each The gradient times were as listed in TABLE 1.

TABLE 1

Gradient times for RP-HPLC method

| Gradient Time | % A | % B |
|---|---|---|
| 0-1 | 95 | 5 |
| 2 | 70 | 30 |
| 54 | 60 | 40 |
| 55.1-70 | 95 | 5 | dSEC-HPLC (AB UDB Analysis)

Denaturing SEC-HPLC was conducted as follows. The pretreatment of samples for the denaturing SEC assay involves a reagent/sample mixture at final concentrations of 200 μg/mL of protein, 3 M Guanidine HCl, and 100 mM Tris, at a pH of 7.4. The samples were heated at 80° C. for 20 minutes while mixing through inversion. For this assay, two controls are employed to allow a bracketing of UDB levels. Internal references with low and high levels of UDB were used as controls.

Chromatographic/Assay conditions were as follows:
Column: Tosoh BioSep G3000 SWx1
Column Temp: Ambient
Mobile Phase: 3 M Guanidine HCl, 25 mM $NaPO_4$, pH 6.8
Gradient: Isocratic
Flow rate: 0.5 mL/min
Detection: 280 nm
Run Time: 50 minutes
Injection: Triplicate 50 μL (10 μg)

Example 1

Comparison of Wash Buffers for IRT Removal

In this example, an impure solution containing the anti-Aβ monoclonal antibody AAB was purified by adsorption onto a Protein A column followed by a first wash with a wash buffer containing either $CaCl_2$, $MgCl_2$, NaCl or propylene glycol.

The culture containing the monoclonal antibody was purified at small scale using an rmp Protein A Sepharose™ FF column (8.9 mL) connected to a GE Healthcare ÄKTA FPLC chromatography system. For all the rmp Protein A Sepharose™ FF chromatography steps described in experiment 1, the following conditions were used. (Exceptions are noted in the individual experimental descriptions).

Column dimensions—1.0 cm×11.4 cm
Operational flow rate—150 cm/hr
Equilibration 1—20 mM Tris, 150 mM NaCl, pH 7.5 (5 column volumes)
Flush—20 mM Tris, 150 mM NaCl, pH 7.5 (1 column volume)
Wash 1—Variable (See Table 2) except for run #1, which had no wash 1
Wash 2—20 mM Tris, 1.0 M NaCl, pH 7.5 (5 column volumes)
Wash 3—10 mM Tris, 75 mM NaCl, pH 7.5 (7 column volumes)
Elution—50 mM Glycine, 75 mM NaCl, pH 3.1 (6 column volumes)
Strip 1—20 mM Sodium Citrate, pH 2.7 (5 column volumes)
Strip 2—6 M Guanidine HCl (2 column volumes)
Strip wash—20 mM Tris, 150 mM NaCl, pH 7.5 (5 column volumes)
Storage—16% Ethanol (5 column volumes)
Run temperature: 2-8° C.

The rmp Protein A Sepharose™ FF column runs were equilibrated with 5 column volumes of 20 mM Tris, 150 mM NaCl, pH 7.5. The column was loaded at approximately 10 mg product/mL resin. Loading was followed by a 1 column volume flush with equilibration buffer and 5 column volumes of wash 1 solution. All Wash 1 solutions tested are outlined in Table 2. Wash 1 was included in all runs except for run #1. Wash 1 was followed by 5 column volumes of 20 mM Tris, 1.0 M NaCl, pH 7.5 and 7 column volumes of 10 mM Tris, 75 mM NaCl, pH 7.5. The monoclonal antibody was eluted from the column with 50 mM Glycine, 75 mM NaCl, pH 3.1. The product pool was then neutralized to 7.9-8.1 with 2 M Tris pH 8.5. The columns were then stripped, washed and stored. Table 2 lists the levels of the IRT species & LMW present in the product pools from the various runs. Magnesium chloride and calcium chloride washes reduced levels of IRT and LMW species.

TABLE 2

IRT and LMW Values for Various Wash 1 Buffers

| Run # | Condition | % LMW | % IRT |
|---|---|---|---|
| 1 | Control (No Wash 1) | 4.4 | 2.5 |
| 2 | 20% Propylene Glycol, pH 7.5 | 4.7 | 2.5 |
| 3 | 50 mM Tris, 2.0 M Magnesium Chloride, pH 7.5 | 1.6 | 1.5 |
| 4 | 50 mM Tris, 2.5 M Magnesium Chloride, pH 7.5 | 1.5 | 1.3 |
| 5 | 50 mM Acetate, 2.0 M Magnesium Chloride, pH 4.5 | 0.9 | 0.8 |
| 6 | 50 mM Tris, 4.0 M Sodium Chloride, pH 7.5 | 4.4 | 2.5 |
| 7 | 50 mM Tris, 2.0 M Calcium Chloride, pH 7.5 | 1.8 | 1.4 |
| 8 | 50 mM Tris, 2.5 M Calcium Chloride, pH 7.5 | 0.8 | 0.8 |

The results showed that the magnesium chloride and calcium chloride washes reduced levels of IRT and LMW species, whereas the sodium chloride and propylene glycol washes did not reduce IRT or LMW species.

Example 2

Protein A Chromatography with $CaCl_2$ Wash for IRT Removal

In this example, a larger scale antibody purification was carried out using Protein A chromatography with a $CaCl_2$ wash to remove IRT species.

The culture containing the monoclonal antibody was purified at pilot scale using a MabSelect Protein A column (2.4 L) connected to a Millipore K-Prime 400 chromatography system. The two MabSelect runs were performed as described below.

Column dimensions—13 cm×18 cm
Operational flow rate—150 cm/hr, 300 cm/hr
Equilibration 1—20 mM Tris, 150 mM NaCl, pH 7.5 (5 column volumes)
Flush—20 mM Tris, 150 mM NaCl, pH 7.5 (2 column volumes)
Wash 1—50 mM Tris, 2 M $CaCl_2$, pH 7.5 for run #1 and no wash 1 for run #2
Wash 2—20 mM Tris, 1.0 M NaCl, pH 7.5 (5 column volumes)
Wash 3—10 mM Tris, 75 mM NaCl, pH 7.5 (5 column volumes)
Elution—50 mM Glycine, 25 mM NaCl, pH 3.1 (6 column volumes)
Strip 1—50 mM Glycine, 0.5 M NaCl, pH 2.7 (5 column volumes)
Strip 2—6 M Guanidine HCl (2 column-volumes)
Strip wash—20 mM Tris, 150 mM NaCl, pH 7.5 (5 column volumes)
Storage—16% Ethanol (5 column volumes)
Run temperature: 2-8° C.

The MabSelect Protein A column was equilibrated with 5 column volumes of 20 mM Tris, 150 mM NaCl, pH 7.5. The columns were then loaded at approximately 10 mg product/mL resin. This was followed by a 2 column volume flush with equilibration buffer and 5 column volumes of wash 1 solution. This wash 1 solution consisted of 50 mM Tris, 2.0 M $CaCl_2$, pH 7.5 for run 1, while it was left out entirely for run 2. Wash 1 was then followed by 5 column volumes of 50 mM Tris, 1.0 M NaCl, pH 7.5 and 5 column volumes of 10 mM Tris, 75 mM NaCl, pH 7.5. The monoclonal antibody was eluted from the MabSelect Protein A column with 50 mM Glycine, 25 mM NaCl, pH 3.1. The product pool was then neutralized to 7.8-8.2 with 2 M Tris pH 8.5. The columns were then stripped, washed and stored. The results are shown in Table 3.

TABLE 3

| % IRT levels in pilot-scale runs with and without calcium chloride wash | | |
|---|---|---|
| Run # | Wash 1 Buffer | % IRT |
| 1 | 50 mM Tris, 2 M $CaCl_2$, pH 7.5 | 0.8 |
| 2 | Control (None) | 1.9 |

The results showed that at pilot scale the calcium chloride wash removed IRT from the product pool.

Example 3

DNA Removal

In this example, the ability of a $CaCl_2$ wash to remove host cell DNA from a preparation containing the AB monoclonal antibody was examined.

The culture containing the monoclonal antibody was purified at small scale using a MabSelect Protein A column (19 mL) connected to a GE Healthcare ÄKTA FPLC chromatography system. The three MabSelect runs were performed as described below.

Column dimensions—1.1 cm×20 cm
Operational flow rate—300 cm/hr
Equilibration 1—20 mM Tris, 150 mM NaCl, pH 7.5 (5 column volumes)
Flush—20 mM Tris, 150 mM NaCl, pH 7.5 (2 column volumes)
Wash 1—50 mM Tris, 2.0 M $CaCl_2$, pH 7.5 (5 column volumes) (Runs 2 and 3 only)
Wash 2—20 mM Tris, 1.0 M NaCl, pH 7.5 (5 column volumes) (Runs 1 and 3 only)
Wash 3—10 mM Tris, 75 mM NaCl, pH 7.5 (7 column volumes)
Elution—50 mM Glycine, 75 mM NaCl, pH 3.0 (6 column volumes)
Strip—50 mM Glycine, 0.5 M NaCl, pH 2.7 (5 column volumes)
Strip wash—20 mM Tris, 150 mM NaCl, pH 7.5 (5 column volumes)
Storage—16% Ethanol (5 column volumes)
Run temperature: 18-24° C.

The MabSelect Protein A column runs were equilibrated with 5 column volumes of 20 mM Tris, 150 mM NaCl, pH 7.5. The columns were then loaded at a load of approximately 40 mg product/mL resin. This was followed by a 2 column volume flush with equilibration buffer. For runs 2 and 3, this step was followed by 5 column volumes of Wash 1 solution. For runs 1 and 3, 5 column volumes of Wash 2 solution was used. All 3 runs employed 7 column volumes of Wash 3 solution. The monoclonal antibody was eluted off the MabSelect Protein A column with 50 mM Glycine, 75 mM NaCl, pH 3.0. The product pool was then neutralized to 7.5-8.0 with 2 M Tris pH 8.5. The columns were then stripped, washed and stored. The results are shown in Table 4.

TABLE 4

| DNA removal with calcium chloride wash. | | | |
|---|---|---|---|
| Run # | Wash 1 | Wash 2 | DNA (ng/mL) | DNA (ppm) |
| 1 | None (Control) | 20 mM Tris, 1 M NaCl, pH 7.5 | 3.6 | 0.37 |
| 2 | 50 mM Tris, 2 M $CaCl_2$, pH 7.5 | None | 0.9 | 0.09 |
| 3 | 50 mM Tris, 2 M $CaCl_2$, pH 7.5 | 20 mM Tris, 1 M NaCl, pH 7.5 | 0.3 | 0.03 |

The results showed that the addition of 50 mM Tris, 2.0 M calcium chloride, pH 7.5, provided 10 fold greater reduction of DNA compared to using NaCl in the wash solution.

Example 4

Host Cell Protein Removal

In this example, a second anti-Aβ monoclonal antibody, 12A11, was used in purification runs in which various wash conditions were tested for the ability to remove host cell proteins (HCP).

A high throughput screen (HTS) in a 96-well filter plate format was performed to identify the best wash conditions for removal of impurities such as HCP for the MabSelect step. This screen varied the wash excipients, excipient concentration, and pH to determine their effect on process related impurities such as HCP.

The MabSelect resin was equilibrated using 5 mM Tris, 10 mM NaCl, pH 7.3 and loaded with product in a column. The resin was then unpacked, mixed and 50 μL of resin was distributed to each well of a 96 well filter plate. The resin in each well was equilibrated in solution of 5 mM Tris, 10 mM NaCl, pH 7.3, and then washed with each of the various excipient wash solutions in 3 stages, each using 300 μL of wash buffer. After the excipient wash, a second wash with 5 mM Tris, 10 mM NaCl, pH 7.3 buffer was performed in 4 stages of 300 μL each. The product was then eluted from the resin in 3 stages of 300 μL each. Elution stages 1 and 2 were combined and tested for HCP levels.

Resin Volume—50 μL
Wash Excipients—Sodium Chloride, Calcium Chloride, Magnesium Chloride,
Excipient Concentrations—100, 250, 500, 1000, 1500, and 2000 mM
Excipient pH—6.0 & 7.5
Elution Buffers—25 mM Hepes, 10 mM NaCl, pH 3.0, 25 mM Hepes, 100 mM NaCl, pH 3.0, 50 mM Glycine, 10 mM NaCl, pH 3.0, 50 mM Glycine, 100 mM NaCl, pH 3.0 and 100 mM Arginine, 10 mM NaCl, pH 3.0, 100 mM Arginine, 100 mM NaCl, pH 3.0
Run temperature: 18-24° C.

The results are shown in Table 5 and Table 6.

TABLE 5

HCP values for MabSelect resin washed with sodium chloride, calcium chloride, or magnesium chloride at pH 6.0

| Elution Buffer | Elution NaCl Conc. (mM) | Wash Excipient Conc. (mM) | Wash Excipient NaCl | Wash Excipient $CaCl_2$ | Wash Excipient $MgCl_2$ |
| --- | --- | --- | --- | --- | --- |
| | | | HCP (ppm) | | |
| 50 mM Glycine | 10 | 100 | 46,800 | 28,500 | 30,800 |
| 25 mM HEPES | | 250 | 35,300 | 17,900 | 22,000 |
| 100 mM Arginine | | 500 | 40,900 | 17,700 | 18,400 |
| 50 mM Glycine | | 1000 | 34,300 | 12,600 | 14,200 |
| 25 mM HEPES | | 1500 | 37,000 | 7,800 | 10,700 |
| 100 mM Arginine | | 2000 | 43,900 | 5,800 | 9,300 |

TABLE 6

HCP values for MabSelect resin washed with sodium chloride, calcium chloride, or magnesium chloride at pH 7.5.

| Elution Buffer | Elution NaCl Conc. (mM) | Wash Excipient Conc. (mM) | Wash Excipient NaCl | Wash Excipient $CaCl_2$ | Wash Excipient $MgCl_2$ |
| --- | --- | --- | --- | --- | --- |
| | | | HCP (ppm) | | |
| 50 mM Glycine | 100 | 100 | 27,900 | 17,900 | 21,800 |
| 25 mM HEPES | | 250 | 24,700 | 16,600 | 18,200 |
| 100 mM Arginine | | 500 | 26,500 | 14,000 | 17,300 |
| 50 mM Glycine | | 1000 | 30,100 | 14,500 | 17,700 |
| 25 mM HEPES | | 1500 | 35,300 | 12,000 | 12,500 |
| 100 mM Arginine | | 2000 | 41,700 | 8,200 | 11,700 |

The results showed that both calcium chloride and magnesium chloride reduced the level of HCP in the MabSelect peak pool compared to sodium chloride at pH 6.0 (Table 5) and pH 7.5 (Table 6).

Example 5

Removal of Under-Disulfide Bonded Species (UDB)

In this example, the ability of the $CaCl_2$ wash to remove under disulfide bonded species (UDB) was examined.

Two rmp Protein A Sepharose™ FF runs were performed essentially as described in example 1.

Column dimensions—1.0 cm×11.4 cm
Operational flow rate—150 cm/hr
Equilibration 1—20 mM Tris, 150 mM NaCl, pH 7.5 (5 column volumes)
Flush—20 mM Tris, 150 mM NaCl, pH 7.5 (1 column volume)
Wash 1—50 mM Acetate, 2.0 M $CaCl_2$, pH 5.0 for Run 1; None for Run 2
Wash 2—20 mM Tris, 1.0 M NaCl, pH 7.5 (5 column volumes)
Wash 3—10 mM Tris, 75 mM NaCl, pH 7.5 (7 column volumes)
Elution—50 mM Glycine, 75 mM NaCl, pH 3.1 (6 column volumes)
Strip 1—20 mM Sodium Citrate, pH 2.7 (5 column volumes)
Strip 2—6 M Guanidine HCl (2 column volumes)
Strip wash—20 mM Tris, 150 mM NaCl, pH 7.5 (5 column volumes)
Storage—16% Ethanol (5 column volumes)
Run temperature: 2-8° C.

The rmp Protein A Sepharose FF columns were equilibrated with 5 column volumes of 20 mM Tris, 150 mM NaCl, pH 7.5. The columns were then loaded at a load of approximately 10 mg product/mL resin. This was followed by a 1 column volume flush with equilibration buffer and then 5 column volumes of wash 1 solution. This wash 1 solution consisted of 50 mM Acetate, 2.0 M $CaCl_2$, pH 5.0 for run 1, while it was left out entirely for run 2. Wash 1 was then followed by 5 column volumes of 20 mM Tris, 1.0 M NaCl, pH 7.5 and 7 column volumes of 10 mM Tris, 75 mM NaCl, pH 7.5. The monoclonal antibody was eluted off the rmp Protein A Sepharose™ FF column with 50 mM Glycine, 75 mM NaCl, pH 3.1. The product pool was then neutralized to 7.8-8.2 with 2 M TrispH 8.5. The columns were then stripped, washed and stored. The results are shown in Table 7.

TABLE 7

% UDB for with and without calcium washed samples.

| Run # | Sample | % UDB |
| --- | --- | --- |
| 1 | 50 mM Acetate, 2.0 M $CaCl_2$, pH 5.0 | 9.5 |
| 2 | None (Control) | 20.8 |

A 2-fold reduction in UDB levels was observed for the run that had the additional 50 mM Acetate, 2.0 M $CaCl_2$, pH 5.0 wash.

Example 6

Removal of HCP and IRT with other Divalent Cation Salt Washes

In this example, the ability of washes containing either $MnCl_2$ or $NiCl_2$ to remove impurities from a preparation containing the anti-Aβ monoclonal antibody AAB was examined.

Two runs were performed to evaluate the effect of washes containing other divalent cationic salts such as $MnCl_2$ and $NiCl_2$. Two control runs were also performed—one using a 50 mM Tris, 1.0 M NaCl, pH 7.5 wash (no IRT or HCP removal expected) and another using a 50 mM Tris, 2.0 M $CaCl_2$, pH 7.5 wash.

The culture containing the monoclonal antibody was purified at small scale using a MabSelect Protein A column (9 mL) connected to a GE Healthcare ÄKTA FPLC chromatography system. The MabSelect runs were performed as described below. As described below, all operational parameters were identical for the four runs except for Wash 1, which was variable (Table 8).

Column dimensions—1.0 cm×11.5 cm (9 mL)
Operational flow rate—300 cm/hr (Equilibration, Wash 2, Elution, Regeneration, Storage)
Operational flow rate—230 cm/hr (Load, Flush, Wash 1)
Equilibration 1—50 mM Tris, 150 mM NaCl, pH 7.5 (5.0 column volumes)
Wash 1—Variable (See Table 8 for composition)
Wash 2—50 mM Tris, 10 mM NaCl, pH 7.5 (5 column volumes)
Elution—50 mM Glycine, 10 mM NaCl, pH 3.0 (3 column volumes)
Regeneration—50 mM NaOH, 0.5 M $Na_2SO_4$ (5 column volumes)
Storage—16% Ethanol, 50 mM Tris, 150 mM NaCl, pH 7.5 (5 column volumes)
Run temperature: 18-24° C.

The MabSelect Protein A column was equilibrated with 5 column volumes of 50 mM Tris, 150 mM NaCl, pH 7.5. The column was loaded at approximately 40 mg product/mL resin. The remaining load was flushed out of the column with 5 column volumes of 50 mM Tris, 150 mM NaCl pH 7.5. The column was then washed with one of the solutions described in Table 11. Prior to elution the column was washed with 5 column volumes of 50 mM Tris, 10 mM NaCl, pH 7.5. The product was eluted from the MabSelect Protein A column with 50 mM Glycine, 10 mM NaCl, pH 3.0. The product pool was then neutralized to pH 8.0 with 2 M Tris pH 9.0. The column was stripped with 5 column volumes 50 mM NaOH, 0.5 M Na2SO4 then stored with 5 column volumes of 16% ethanol, 50 mM Tris, 150 mM NaCl, pH 7.5. The results are shown in Table 8 (HCP removal) and Table 9 (IRT removal).

TABLE 8

| HCP removal with various wash solutions | | |
| --- | --- | --- |
| Run # | Wash 1 Condition | HCP (PPM) |
| 1 | 50 mM Tris, 1.0 M NaCl, pH 7.5 | 17,600 |
| 2 | 50 mM Sodium Acetate, 1.5 M $MnCl_2$, pH 5.0* | 10,600 |
| 3 | 50 mM Sodium Acetate, 1.5 M $NiCl_2$, pH 5.0* | 4,700 |
| 4 | 50 mM Tris, 2.0 M $CaCl_2$, pH 7.5 | 6,500 |

*pH 5.0 was chosen due to solubility of $MnCl_2$ and $NiCl_2$

TABLE 9

| IRT Removal with various wash solutions | | |
| --- | --- | --- |
| Run # | Wash 1 Condition | IRT (%) |
| 1 | 50 mM Tris, 1.0 M NaCl, pH 7.5 | 2.78 |
| 2 | 50 mM Sodium Acetate, 1.5 M $MnCl_2$, pH 5.0* | 0.77 |
| 3 | 50 mM Sodium Acetate, 1.5 M $NiCl_2$, pH 5.0* | 0.47 |
| 4 | 50 mM Tris, 2.0 M $CaCl_2$, pH 7.5 | 0.87 | pH 5.0 was chosen due to solubility of $MnCl_2$ and $NiCl_2$

Table 8 shows that the level of HCPs present in runs that were washed with solutions containing divalent cations had 1.5-3.5 fold less HCPs than the control (1.0 M NaCl Wash). Table 9 shows that the runs that contained the washes with divalent cationic salts solutions also provide >3.5 fold IRT removal compared to the run with a 1.0 M NaCl containing wash solutions. Thus, these results demonstrated that salt washes with other divalent cations (e.g., with $MnCl_2$ or $NiCl_2$), different than $CaCl_2$, also were effective in removing impurities.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for purifying an Aβ binding protein having an Fc region from a source liquid comprising the protein and one or more impurities, wherein the Aβ binding protein is an anti-Aβ antibody, comprising the steps of:
   adsorbing the Aβ binding protein to an Fc binding agent;
   washing the Fc binding agent bound to the Aβ binding protein with a buffer solution containing CaCl$_2$ at a concentration from about 0.5 M to about 3 M to reduce the one or more impurities; and
   recovering the Aβ binding protein from the Fc binding agent in an elution solution.

2. The method of claim 1, wherein said one or more impurities are selected from the group consisting of: intron read through variant species (IRT), under disulfide bonded species (UDB) and low molecular weight species (LMW).

3. The method of claim 2, wherein said one or more impurities is an IRT.

4. The method of claim 1, wherein the antibody is selected from the group consisting of: an antibody fusion, a murine antibody, a chimeric antibody, a humanized antibody and a human antibody.

5. The method of claim 1, wherein the Aβ binding protein having an Fc region is recombinantly produced.

6. The method of claim 1, wherein the Aβ binding protein having an Fc region is recombinantly produced in a Chinese Hamster Ovary (CHO) cell.

7. The method of claim 1, wherein the Fc binding agent comprises one or more of Protein A and Protein G.

8. The method of claim 1, wherein the Fc binding agent is immobilized on a solid phase.

9. The method of claim 8, wherein the solid phase comprises one or more of a bead, a gel, a resin, and a particle.

10. The method of claim 1, wherein the buffer solution containing the CaCl$_2$ has a pH value in a range between about 4 to about 8.

11. The method of claim 1, wherein the buffer solution containing the CaCl$_2$ has a pH value in a range between about 7.3 to about 7.7.

12. The method of claim 1, wherein the buffer solution has a CaCl$_2$ concentration in a range between about 1 M to about 3 M.

13. The method of claim 12, wherein the buffer solution has a CaCl$_2$ concentration in a range between about 1.5 M to about 2.0 M.

14. The method of claim 1, wherein the buffer solution containing CaCl$_2$ comprises at 1 ast about 1.5 M to about 2.5 M CaCl$_2$.

15. The method of claim 1, wherein the buffer solution containing CaCl$_2$ comprises about 2 M CaCl$_2$.

16. The method of claim 1, wherein the steps of adsorbing the Aβ binding protein to an Fc binding agent and washing the Fc binding agent are performed at a temperature in the range between about 2° C. to about 24° C.

17. The method of claim 1, wherein the one or more impurities comprise one or more of a host cell protein, a host cell DNA, a cell culture protein, and mixtures thereof.

18. The method of claim 1, wherein the one or more impurities comprise an undesired species of the protein having an Fc region.

19. The method of claim 18, wherein the undesired species of the Aβ binding protein comprises one or more of antibody chains or fragments thereof having an intronic read through sequence, one or more antibody chains or fragments thereof having an improper disulfide linkage, a half-antibody or fragment thereof, a light chain dimer or fragment thereof, and a heavy chain dimer or fragment hereof.

20. The method of claim 1, wherein the step of recovering the Aβ binding protein from the Fc binding agent comprises eluting the protein using an elution buffer having a pH in a range from about 2.0 to about 6.5.

21. The method of claim 20, wherein the elution buffer has a pH in a range from about 2.0 to about 4.0.

22. The method of claim 1, wherein the method further comprises a chromatography step selected from the group consisting of: anion exchange chromatography, cation exchange chromatography, immobilized metal affinity chromatography and hydrophobic interaction chromatography (HIC).

23. The method of claim 1, wherein the method further comprises an additional purification step selected from the group consisting of hydroxyapatite chromatography, dialysis, affinity chromatography, ammonium sulphate precipitation, ethanol precipitation, reverse phase HPLC (RP-HPLC), and chromatofocusing.

24. The method of claim 1, wherein the one or more impurities comprise one or more intron read-through variants of the protein and the elution solution containing the protein has a level of intron read-through variants that is at least 5 fold less than the level of intron read-through variants in the source liquid.

25. The method of claim 24, wherein a solution containing the protein recovered in the elution solution has a level of intron read-through variants that is at least 10 fold less than the level of intron read-through variants in the source liquid.

26. The method of claim 1, wherein the one or more impurities comprise one or more intron read-through variants of the protein and the intron read-through variants comprise less than about 1% of a species of said protein in the elution solution.

27. The method of claim 26, wherein the intron read-through variants comprise less than about 0.8% of a species of said protein in the elution solution.

28. The method of claim 27, wherein the intron read-through variants comprise less than about 0.5% of the species of said protein in the elution solution.

29. The method of claim 28, wherein the intron read-through variants comprise less than about 0.2% of a species of said protein in the elution solution.

30. The method of claim 1, wherein the one or more impurities comprise one or more low molecular weight species of the protein and the low molecular weight species comprise less than about 1% of a species of said protein in the elution solution.

31. The method of claim 30, wherein the low molecular weight species comprise less than about 0.8% of a species of said protein in the elution solution.

32. The method of claim 31, wherein the low molecular weight species comprise less than about 0.5% of a species of said protein in the elution solution.

33. The method of claim 32, wherein the low molecular weight species comprise less than about 0.2% of a species of said protein in the elution solution.

34. The method of claim 1, wherein the one or more impurities comprise one or more under-disulfide bonded variants of the protein and the under-disulfide bonded variants comprise less than about 15% of a species of said protein in the elution solution.

35. The method of claim 34, wherein the under-disulfide bonded variants comprise less than about 10% of a species of said protein in the elution solution.

36. The method of claim 35, wherein the under-disulfide bonded variants comprise less than about 5% of a species of said protein in the elution solution.

37. The method of claim 36, wherein the under-disulfide bonded variants comprise less than about 2% of a species of said protein in the elution solution.

38. The method of claim 1, wherein the Fc binding agent is a moiety that binds selectively or preferentially to the Fc region of the antibody in the source liquid.

39. The method of claim 1, further comprising washing the Fc binding agent bound to the Aβ binding protein with a buffer solution containing NaCl at a concentration of at least about 10 mM after washing with the $CaCl_2$.

40. The method of claim 1, wherein the one or more impurities comprise one or more of an intron read-through variant species (IRT), an under disulfide-bonded species (UDB), and a low molecular weight species (LMW), and the one or more impurities is reduced to a level of at least about 2-fold lower than that present in the source liquid.

41. A method for purifying an Aβ binding protein having an Fc region from a source liquid comprising the Aβ binding protein and one or more impurities, wherein the Aβ binding protein is a humanized 3D6 antibody and wherein the one or more impurities comprise one or more intron read through variant species (IRT), the method comprising the steps of:
adsorbing the Aβ binding protein to an affinity ligand which is an Fc binding agent;
washing the affinity ligand with a buffer solution containing $CaCl_2$ at a concentration from about 0.5 M to about 3 M to reduce the IRT; and
recovering the Aβ binding protein from the affinity ligand in an elution solution, wherein the Aβ binding protein having an Fc region is purified from the source liquid.

42. The method of claim 41, wherein the buffer solution containing the $CaCl_2$ has a pH value in a range between about 4 to about 8.

43. The method of claim 41, wherein the buffer solution containing the $CaCl_2$ has a pH value in a range between about 7.3 to about 7.7.

44. The method of claim 41, wherein the buffer solution has a $CaCl_2$ concentration in a range between about 1 M to about 3 M.

45. The method of claim 44, wherein the buffer solution has a $CaCl_2$ concentration in a range between about 1.5 M to about 2.5 M.

46. The method of claim 41, wherein the buffer solution containing the $CaCl_2$ comprises about 2 M $CaCl_2$.

47. The method of claim 41, wherein the Aβ binding protein having an Fc region is recombinantly produced.

48. The method of claim 47, wherein the Aβ binding protein having an Fc region is recombinantly produced in a Chinese Hamster Ovary (CHO) cell.

49. The method of claim 41, wherein the Fc binding agent comprises one or more of Protein A and Protein G.

50. The method claim 41, wherein the Fc binding agent is immobilized on a solid phase.

51. The method of claim 41, wherein the steps of adsorbing the Aβ binding protein to an Fc binding agent and washing the Fc binding agent are performed at a temperature in the range between about 2° C. to about 24° C.

52. The method of claim 41, wherein the step of recovering the Aβ binding protein from the Fc binding agent comprises eluting the protein using an elution buffer having a pH in a range from about 2.0 to about 6.5.

53. The method of claim 52, wherein the elution buffer has a pH in a range from about 2.0 to about 4.0.

54. The method of claim 41, wherein the method further comprises a chromatography step selected from the group consisting of: anion exchange chromatography, cation exchange chromatography, immobilized metal affinity chromatography and hydrophobic interaction chromatography (HIC).

55. The method of claim 41, wherein the method further comprises an additional purification step selected from the group consisting of: hydroxyapatite chromatography, dialysis, affinity chromatography, ammonium sulphate precipitation, ethanol precipitation, reverse phase HPLC (RP-HPLC), and chromatofocusing.

56. The method of claim 41, wherein the elution solution containing the Aβ binding protein has a level of intron read-through variants that is at least 5 fold less than the level of intron read-through variants in the source liquid.

57. The method of claim 41, wherein the intron read-through variants comprise less than about 1% of a species of said protein in the elution solution.

58. The method of claim 41, wherein the affinity ligand is a moiety that binds selectively or preferentially to the Fc region of the antibody in the source liquid.

59. The method of claim 41, wherein the impurities further comprise at least one of under disulfide bonded species (UDB) and low molecular weight species (LMW).

60. The method of claim 41, wherein the one or more impurities comprise one or more of an intron read-through variant species (IRT), an under disulfide-bonded species (UDB), and a low molecular weight species (LMW), and the one or more impurities is reduced to a level of at least about 2-fold lower than that present in the source liquid.

61. The method of claim 41, further comprising washing the Fc binding agent bound to the Aβ binding protein with a buffer solution containing NaCl at a concentration of at least about 10 mM after washing with $CaCl_2$.

62. The method of claim 41, wherein the humanized 3D6 antibody comprises a light chain comprising the amino acid sequence of SEQ ID NO:1 and a heavy chain comprising the amino acid sequence of SEQ ID NO:2.

63. The method of claim 41, wherein the humanized 3D6 antibody comprises a light chain comprising the amino acid sequence of SEQ ID NO:1 and a heavy chain comprising the amino acid sequence of residues 1-448 of SEQ ID NO:2.

64. The method of claim 41, wherein the humanized 3D6 antibody is of isotype IgM, IgG1, IgG2, IgG3, or IgG4.

65. The method of claim 64, wherein the humanized 3D6 antibody is of isotype human IgG1.

66. A method for purifying an Aβ binding protein having an Fc region from a source liquid comprising the protein and one or more impurities, wherein the Aβ binding protein is a humanized anti-Aβ antibody, the method comprising the steps of:
adsorbing the Aβ binding protein to an affinity ligand which is an Fc binding agent;
washing the affinity ligand with a buffer solution containing $CaCl_2$ at a concentration from about 0.5 M to about 3 M to reduce the one or more impurities; and
recovering the Aβ binding protein from the affinity ligand in an elution solution.

67. The method of claim 66, wherein said one or more impurities are selected from the group consisting of: intron read through variant species (IRT), under disulfide bonded species (UDB) and low molecular weight species (LMW).

68. The method of claim 66, wherein the antibody is selected from the group consisting of: 3D6, 10D5, 12A11, 266, 15C11, and 12B4.

69. The method of claim 66, wherein the Aβ binding protein having an Fc region is recombinantly produced.

70. The method of claim 69, wherein the Aβ binding protein having an Fc region is recombinantly produced in a Chinese Hamster Ovary (CHO) cell.

71. The method of claim 66, wherein the Fc binding agent comprises one or more of Protein A and Protein G.

72. The method of claim 66, wherein the Fc binding agent is immobilized on a solid phase.

73. The method of claim 66, wherein the buffer solution containing the $CaCl_2$ has a pH value in a range between about 4 to about 8.

74. The method of claim 66, wherein the buffer solution containing the $CaCl_2$ has a pH value in a range between about 7.3 to about 7.7.

75. The method of claim 66, wherein the buffer solution has a $CaCl_2$ concentration in a range between about 1 M to about 3 M.

76. The method of claim 66, wherein the buffer solution containing $CaCl_2$ comprises at least about 1.5 M to about 2.5 M $CaCl_2$.

77. The method of claim 66, wherein the buffer solution containing $CaCl_2$ comprises about 2 M $CaCl_2$.

78. The method of claim 66, wherein the steps of adsorbing the Aβ binding protein to an Fc binding agent and washing the Fc binding agent are performed at a temperature in the range between about 2° C. to about 24° C.

79. The method of claim 66, wherein the one or more impurities comprise one or more of a host cell protein, a host cell DNA, a cell culture protein, and mixtures thereof.

80. The method of claim 66, wherein the one or more impurities comprise an undesired species of the protein having an Fc region.

81. The method of claim 80, wherein the undesired species of the Aβ binding protein comprises one or more of antibody chains or fragments thereof having an intronic read through sequence, one or more antibody chains or fragments thereof having an improper disulfide linkage, a half-antibody or fragment thereof, a light chain dimer or fragment thereof, and a heavy chain dimer or fragment thereof.

82. The method of claim 66, wherein the step of recovering the Aβ binding protein from the Fc binding agent comprises eluting the protein using an elution buffer having a pH in a range from about 2.0 to about 6.5.

83. The method of claim 81, wherein the elution buffer has a pH in a range from about 2.0 to about 4.0.

84. The method of claim 66, wherein the method further comprises a chromatography step selected from the group consisting of: anion exchange chromatography, cation exchange chromatography, immobilized metal affinity chromatography and hydrophobic interaction chromatography (HIC).

85. The method of claim 66, wherein the method further comprises an additional purification step selected from the group consisting of: hydroxyapatite chromatography, dialysis, affinity chromatography, ammonium sulphate precipitation, ethanol precipitation, reverse phase HPLC (RP-HPLC), and chromatofocusing.

86. The method of claim 66, wherein the one or more impurities comprise one or more intron read-through variants of the protein and the elution solution containing the protein has a level of intron read-through variants that is at least 5 fold less than the level of intron read-through variants in the source liquid.

87. The method of claim 66, wherein the one or more impurities comprise one or more intron read-through variants of the protein and the intron read-through variants comprise less than about 1% of a species of said protein in the elution solution.

88. The method of claim 66, wherein the one or more impurities comprise one or more low molecular weight species of the protein and the low molecular weight species comprise less than about 1% of a species of said protein in the elution solution.

89. The method of claim 66, wherein the one or more impurities comprise one or more under-disulfide bonded variants of the protein and the under-disulfide bonded variants comprise less than about 15% of a species of said protein in the elution solution.

90. The method of claim 66, wherein the affinity ligand is a moiety that binds selectively or preferentially to the Fc region of the antibody in the source liquid.

91. The method of claim 66, further comprising washing the Fc binding agent bound to the Aβ binding protein with a buffer solution containing NaCl at a concentration of at least about 10 mM after washing with the $CaCl_2$.

92. The method of claim 66, wherein the one or more impurities comprise one or more of an intron read-through variant species (IRT), an under disulfide-bonded species (UDB), and a low molecular weight species (LMW), and the one or more impurities is reduced to a level of at least about 2-fold lower than that present in the source liquid.

93. The method of claim 66, further comprising washing the affinity ligand with a buffer solution containing NaCl at a concentration of from 0.75 mM to 2.0 mM prior to recovering the Aβ binding protein.

94. The method of claim 66, wherein the humanized antibody is of isotype IgM, IgG1, IgG2, IgG3, or IgG4.

95. The method of claim 94, wherein the humanized antibody is of isotype human IgG1.

96. A method for purifying an Aβ binding protein having an Fc region from a source liquid comprising the Aβ binding protein and one or more impurities, the method comprising the steps of:

adsorbing the Aβ binding protein to an Fc binding agent comprising Protein A, wherein the Aβ binding protein is a humanized 3D6 antibody comprising a light chain comprising the amino acid sequence of SEQ ID NO:1 and a heavy chain comprising the amino acid sequence of residues 1-448 of SEQ ID NO:2;

washing the Fc binding agent bound to the Aβ binding protein with a buffer solution containing $CaCl_2$ at a concentration of from about 1.5 M to about 2 M to reduce the one or more impurities; and recovering the Aβ binding protein from the Fc binding agent using an elution buffer having a pH in a range from about 2.5 to about 3.5, wherein the Aβ binding protein having an Fc region is purified from the source liquid.

* * * * *

UNITED STATES PATENT AND TRADEMARK OFFICE
CERTIFICATE OF CORRECTION

PATENT NO.       : 7,825,223 B2  
APPLICATION NO.  : 11/454772  
DATED            : November 2, 2010  
INVENTOR(S)      : Ranganathan Godavarti and Timothy Iskra Page 1 of 1

It is certified that error appears in the above-identified patent and that said Letters Patent is hereby corrected as shown below:

Claim 83, Column 98, Line 38, delete "81" and insert --82--

Signed and Sealed this
Fifteenth Day of May, 2012

David J. Kappos
*Director of the United States Patent and Trademark Office*

UNITED STATES PATENT AND TRADEMARK OFFICE
CERTIFICATE OF CORRECTION

PATENT NO. : 7,825,223 B2  Page 1 of 1
APPLICATION NO. : 11/454772
DATED : November 2, 2010
INVENTOR(S) : Ranganathan Godavarti and Timothy Iskra It is certified that error appears in the above-identified patent and that said Letters Patent is hereby corrected as shown below:

In the Claims

Claim 14, Column 94, Line 42, delete "at 1 ast"

Signed and Sealed this
Twenty-second Day of July, 2014

Michelle K. Lee
*Deputy Director of the United States Patent and Trademark Office*

SEQUENCE LISTING

<160> NUMBER OF SEQ ID NOS: 47

<210> SEQ ID NO 1
<211> LENGTH: 219
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Asp Val Val Met Thr Gln Ser Pro Leu Ser Leu Pro Val Thr Pro Gly
1               5                   10                  15

Glu Pro Ala Ser Ile Ser Cys Lys Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 2
<211> LENGTH: 449
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Gly Met Ser Trp Val Arg Gln Ala Pro Gly Lys Gly Leu Glu Trp Val
            35                  40                  45

Ala Ser Ile Arg Ser Gly Gly Gly Arg Thr Tyr Tyr Ser Asp Asn Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
        245                 250                 255
Arg Thr Pro Glu Val Thr Cys Val Val Val Asp Val Ser His Glu Asp
        260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
        325                 330                 335
Thr Ile Ser Lys Ala Lys Gly Gln Pro Arg Glu Pro Gln Val Tyr Thr
        340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
        405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
        435                 440                 445
Lys

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (1)
<223> OTHER INFORMATION: Asp or Tyr
<220> FEATURE:
<221> NAME/KEY: MOD_RES
<222> LOCATION: (7)
<223> OTHER INFORMATION: Ser or Thr
<220> FEATURE:
<221> NAME/KEY: MOD_RES
<222> LOCATION: (10)
<223> OTHER INFORMATION: Ser or Thr
<220> FEATURE:
<221> NAME/KEY: MOD_RES
<222> LOCATION: (15)
<223> OTHER INFORMATION: Leu, Ile, or Val
<220> FEATURE:
<221> NAME/KEY: MOD_RES
<222> LOCATION: (50)
<223> OTHER INFORMATION: Arg or Lys
<220> FEATURE:
```

```
<221> NAME/KEY: MOD_RES
<222> LOCATION: (88)
<223> OTHER INFORMATION: Val or Leu
<220> FEATURE:
<221> NAME/KEY: MOD_RES
<222> LOCATION: (109)
<223> OTHER INFORMATION: Val or Leu

<400> SEQUENCE: 3

Xaa Val Val Met Thr Gln Xaa Pro Leu Xaa Leu Pro Val Thr Xaa Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Xaa Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Trp Gln Gly
                85                  90                  95

Thr His Phe Pro Arg Thr Phe Gly Gly Gly Thr Lys Xaa Glu Ile Lys
            100                 105                 110

Arg

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (3)
<223> OTHER INFORMATION: Gln, Lys, or Arg
<220> FEATURE:
<221> NAME/KEY: MOD_RES
<222> LOCATION: (78)
<223> OTHER INFORMATION: Ser or Thr
<220> FEATURE:
<221> NAME/KEY: MOD_RES
<222> LOCATION: (87)
<223> OTHER INFORMATION: Arg or Lys
<220> FEATURE:
<221> NAME/KEY: MOD_RES
<222> LOCATION: (88)
<223> OTHER INFORMATION: Ala, Ser, or Thr
<220> FEATURE:
<221> NAME/KEY: MOD_RES
<222> LOCATION: (114)
<223> OTHER INFORMATION: Leu, Thr, Ile, or Val

<400> SEQUENCE: 4

Glu Val Xaa Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Xaa Leu Tyr
65                  70                  75                  80
```

-continued

Leu Gln Met Asn Ser Leu Xaa Xaa Glu Asp Thr Ala Val Tyr Tyr Cys
                    85                  90                  95

Val Arg Tyr Asp His Tyr Ser Gly Ser Ser Asp Tyr Trp Gly Gln Gly
            100                 105                 110

Thr Xaa Val Thr Val Ser Ser
        115

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 5

Asp Val Val Met Thr Gln Ser Pro Leu Ser Leu Pro Val Thr Leu Gly
1               5                   10                  15

Glu Pro Ala Ser Ile Ser Cys Lys Ser Gln Ser Leu Leu Asp Ser
            20                  25                  30

Asp Gly Lys Thr Tyr Leu Asn Trp Leu Gln Gln Arg Pro Gly Gln Ser
            35                  40                  45

Pro Arg Arg Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

Arg

<210> SEQ ID NO 6
<211> LENGTH: 119
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
            35                  40                  45

Ala Ser Ile Arg Ser Gly Gly Gly Arg Thr Tyr Tyr Ser Asp Asn Val
50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

```
<210> SEQ ID NO 7
<211> LENGTH: 219
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 7

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Gln Ala Glu Asp Val Gly Val Tyr Tyr Cys Trp Gln Gly
                85                  90                  95

Thr His Phe Pro Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 8
<211> LENGTH: 449
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
```

```
                85                  90                  95
Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 9
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
```

```
<221> NAME/KEY: MOD_RES
<222> LOCATION: (3)
<223> OTHER INFORMATION: Val or Leu
<220> FEATURE:
<221> NAME/KEY: MOD_RES
<222> LOCATION: (7)
<223> OTHER INFORMATION: Ser or Thr
<220> FEATURE:
<221> NAME/KEY: MOD_RES
<222> LOCATION: (14)
<223> OTHER INFORMATION: Thr or Ser
<220> FEATURE:
<221> NAME/KEY: MOD_RES
<222> LOCATION: (17)
<223> OTHER INFORMATION: Gln, Asp, or Asn
<220> FEATURE:
<221> NAME/KEY: MOD_RES
<222> LOCATION: (30)
<223> OTHER INFORMATION: Ile or Val
<220> FEATURE:
<221> NAME/KEY: MOD_RES
<222> LOCATION: (50)
<223> OTHER INFORMATION: Arg or Lys
<220> FEATURE:
<221> NAME/KEY: MOD_RES
<222> LOCATION: (88)
<223> OTHER INFORMATION: Val or Leu
<220> FEATURE:
<221> NAME/KEY: MOD_RES
<222> LOCATION: (105)
<223> OTHER INFORMATION: Gly or Ala
<220> FEATURE:
<221> NAME/KEY: MOD_RES
<222> LOCATION: (109)
<223> OTHER INFORMATION: Val or Leu

<400> SEQUENCE: 9

Asp Val Xaa Met Thr Gln Xaa Pro Leu Ser Leu Pro Val Xaa Leu Gly
1               5                   10                  15

Xaa Pro Ala Ser Ile Ser Cys Arg Ser Ser Gln Asn Ile Xaa His Ser
            20                  25                  30

Asn Gly Asn Thr Tyr Leu Glu Trp Tyr Leu Gln Lys Pro Gly Gln Ser
        35                  40                  45

Pro Xaa Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Phe Gln Gly
                85                  90                  95

Ser His Val Pro Leu Thr Phe Gly Xaa Gly Thr Lys Xaa Glu Ile Lys
            100                 105                 110

Arg

<210> SEQ ID NO 10
<211> LENGTH: 123
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (1)
<223> OTHER INFORMATION: Gln or Glu
<220> FEATURE:
<221> NAME/KEY: MOD_RES
<222> LOCATION: (2)
<223> OTHER INFORMATION: Val or Ala
<220> FEATURE:
<221> NAME/KEY: MOD_RES
```

```
<222> LOCATION: (64)
<223> OTHER INFORMATION: Ser or Thr
<220> FEATURE:
<221> NAME/KEY: MOD_RES
<222> LOCATION: (77)
<223> OTHER INFORMATION: Lys or Arg
<220> FEATURE:
<221> NAME/KEY: MOD_RES
<222> LOCATION: (78)
<223> OTHER INFORMATION: Ser or Thr
<220> FEATURE:
<221> NAME/KEY: MOD_RES
<222> LOCATION: (83)
<223> OTHER INFORMATION: Thr or Ser
<220> FEATURE:
<221> NAME/KEY: MOD_RES
<222> LOCATION: (84)
<223> OTHER INFORMATION: Met, Ile, or Leu
<220> FEATURE:
<221> NAME/KEY: MOD_RES
<222> LOCATION: (86)
<223> OTHER INFORMATION: Asn, Ser, or Thr
<220> FEATURE:
<221> NAME/KEY: MOD_RES
<222> LOCATION: (87)
<223> OTHER INFORMATION: Met, Val, or Leu
<220> FEATURE:
<221> NAME/KEY: MOD_RES
<222> LOCATION: (118)
<223> OTHER INFORMATION: Leu or Ser

<400> SEQUENCE: 10

Xaa Xaa Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Xaa
    50                  55                  60

Leu Lys Ser Arg Leu Thr Ile Ser Lys Asp Thr Ser Xaa Xaa Gln Val
65                  70                  75                  80

Val Leu Xaa Xaa Thr Xaa Xaa Asp Pro Val Asp Thr Ala Thr Tyr Tyr
                85                  90                  95

Cys Val Arg Arg Pro Ile Thr Pro Val Leu Val Asp Ala Met Asp Tyr
            100                 105                 110

Trp Gly Gln Gly Thr Xaa Val Thr Val Ser Ser
        115                 120

<210> SEQ ID NO 11
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 11

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gly Gly Thr Lys Val Glu Ile Lys
            100                 105                 110

Arg

<210> SEQ ID NO 12
<211> LENGTH: 123
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 12

Gln Val Thr Leu Lys Glu Ser Gly Pro Val Leu Val Lys Pro Thr Glu
  1               5                  10                  15

Thr Leu Thr Leu Thr Cys Thr Phe Ser Gly Phe Ser Leu Ser Thr Ser
                 20                  25                  30

Gly Met Gly Val Ser Trp Ile Arg Gln Pro Pro Gly Lys Ala Leu Glu
             35                  40                  45

Trp Leu Ala His Ile Tyr Trp Asp Asp Lys Arg Tyr Asn Pro Ser
 50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Val Arg Arg Pro Ile Thr Pro Val Leu Val Asp Ala Met Asp Tyr
            100                 105                 110

Trp Gln Gln Gly Thr Leu Val Thr Val Ser Ser
            115                 120

<210> SEQ ID NO 13
<211> LENGTH: 219
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 13

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Asn Ile Ile His Ser
                 20                  25                  30

Asn Gly Asn Thr Tyr Leu Glu Trp Tyr Leu Gln Lys Pro Gly Gln Ser
             35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gly Gly Thr Lys Val Glu Ile Lys
            100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
        130                 135                 140

Tyr Pro Arg Gly Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Tyr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

<210> SEQ ID NO 14
<211> LENGTH: 453
<212> TYPE: PRT
<213> ORGANISM: Artificial Sequence
<220> FEATURE:
<223> OTHER INFORMATION: Description of Artificial Sequence: Synthetic
      humanized antibody <400> SEQUENCE: 14

```
Glu Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
 50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Arg Pro Ile Thr Pro Val Leu Val Asp Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Gln Asn Asn Tyr Lys Thr Tyr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 15
<211> LENGTH: 132
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: SIGNAL
<222> LOCATION: (1)..(20)
<220> FEATURE:
<221> NAME/KEY: mat_peptide
<222> LOCATION: (21)..(132)

<400> SEQUENCE: 15

Met Arg Leu Pro Ala Gln Leu Leu Gly Leu Leu Met Leu Trp Val Ser
-20                 -15                 -10                 -5

Gly Ser Ser Gly Asp Val Val Met Thr Gln Ser Pro Leu Ser Leu Pro
            -1  1                   5                  10

Val Thr Pro Gly Glu Pro Ala Ser Ile Ser Cys Arg Ser Ser Gln Asn
        15                   20                  25

Ile Val His Ser Asn Gly Asn Thr Tyr Leu Glu Trp Tyr Leu Gln Lys
    30                  35                  40

Pro Gly Gln Ser Pro Gln Leu Leu Ile Tyr Lys Val Ser Asn Arg Phe
45                  50                  55                  60

Ser Gly Val Pro Asp Arg Phe Ser Gly Ser Gly Ser Gly Thr Asp Phe
                65                  70                  75

Thr Leu Lys Ile Ser Arg Val Glu Ala Glu Asp Val Gly Val Tyr Tyr
            80                  85                  90

Cys Phe Gln Gly Ser His Val Pro Leu Thr Phe Gly Gln Gly Thr Lys
```

-continued

```
                95                  100                 105
Leu Glu Ile Lys
    110

<210> SEQ ID NO 16
<211> LENGTH: 142
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: SIGNAL
<222> LOCATION: (1)..(19)
<220> FEATURE:
<221> NAME/KEY: mat_peptide
<222> LOCATION: (20)..(142)

<400> SEQUENCE: 16

Met Lys His Leu Trp Phe Phe Leu Leu Leu Val Ala Ala Pro Arg Trp
                -15                 -10                 -5

Val Leu Ser Gln Val Gln Leu Gln Glu Ser Gly Pro Gly Leu Val Lys
       -1   1               5                   10

Pro Ser Glu Thr Leu Ser Leu Thr Cys Thr Phe Ser Gly Phe Ser Leu
    15                  20                  25

Ser Thr Asn Gly Met Gly Val Ser Trp Ile Arg Gln Pro Pro Gly Lys
30                  35                  40                  45

Gly Leu Glu Trp Leu Ala His Ile Tyr Trp Asp Glu Asp Lys Arg Tyr
                50                  55                  60

Asn Pro Ser Leu Lys Ser Arg Leu Thr Ile Ser Lys Asp Thr Ser Lys
                65                  70                  75

Asn Gln Val Ser Leu Lys Leu Ser Ser Val Thr Ala Ala Asp Thr Ala
            80                  85                  90

Val Tyr Tyr Cys Ala Arg Arg Ile Ile Tyr Asp Val Glu Asp Tyr
                95                  100                 105

Phe Asp Tyr Trp Gly Gln Gly Thr Thr Val Thr Val Ser Ser
110                 115                 120

<210> SEQ ID NO 17
<211> LENGTH: 131
<212> TYPE: PRT
<213> ORGANISM: Mus musculus
<220> FEATURE:
<221> NAME/KEY: SIGNAL
<222> LOCATION: (1)..(19)
<220> FEATURE:
<221> NAME/KEY: mat_peptide
<222> LOCATION: (20)..(131)

<400> SEQUENCE: 17

Met Lys Leu Pro Val Arg Leu Leu Val Leu Met Phe Trp Ile Pro Ala
                -15                 -10                 -5

Ser Ser Ser Asp Val Leu Met Thr Gln Thr Pro Leu Ser Leu Pro Val
       -1   1               5                   10

Ser Leu Gly Asp Gln Ala Ser Ile Ser Cys Arg Ser Ser Gln Asn Ile
    15                  20                  25

Val His Ser Asn Gly Asn Thr Tyr Leu Glu Trp Tyr Leu Gln Lys Pro
30                  35                  40                  45

Gly Gln Ser Pro Lys Leu Leu Ile Tyr Lys Val Ser Asn Arg Phe Ser
                50                  55                  60

Gly Val Pro Asp Arg Phe Ser Gly Ser Gly Ser Gly Thr Asp Phe Thr
```

```
                    65                  70                  75
Leu Lys Ile Ser Arg Val Glu Ala Glu Asp Leu Gly Val Tyr Tyr Cys
            80                  85                  90

Phe Gln Gly Ser His Val Pro Leu Thr Phe Gly Ala Gly Thr Lys Leu
        95                  100                 105

Glu Leu Lys
110

<210> SEQ ID NO 18
<211> LENGTH: 142
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: SIGNAL
<222> LOCATION: (1)..(19)
<220> FEATURE:
<221> NAME/KEY: mat_peptide
<222> LOCATION: (20)..(142)

<400> SEQUENCE: 18

Met Lys His Leu Trp Phe Phe Leu Leu Leu Val Ala Ala Pro Arg Trp
                -15                 -10                 -5

Val Leu Ser Gln Leu Gln Leu Gln Glu Ser Gly Pro Gly Leu Val Lys
         -1  1               5                   10

Pro Ser Glu Thr Leu Ser Leu Thr Cys Thr Phe Ser Gly Phe Ser Leu
        15                  20                  25

Ser Thr Asn Gly Met Gly Val Ser Trp Ile Arg Gln Pro Pro Gly Lys
30                  35                  40                  45

Gly Leu Glu Trp Ile Gly His Ile Tyr Trp Asp Glu Asp Lys Arg Tyr
                50                  55                  60

Asn Pro Ser Leu Lys Ser Arg Val Thr Ile Ser Lys Asp Thr Ser Lys
            65                  70                  75

Asn Gln Phe Ser Leu Lys Leu Ser Ser Val Thr Ala Ala Asp Thr Ala
        80                  85                  90

Val Tyr Tyr Cys Ala Arg Arg Ile Ile Tyr Asp Val Glu Asp Tyr
    95                  100                 105

Phe Asp Tyr Trp Gly Gln Gly Thr Thr Val Thr Val Ser Ser
110                 115                 120

<210> SEQ ID NO 19
<211> LENGTH: 142
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: SIGNAL
<222> LOCATION: (1)..(19)
<220> FEATURE:
<221> NAME/KEY: mat_peptide
<222> LOCATION: (20)..(142)

<400> SEQUENCE: 19

Met Lys His Leu Trp Phe Phe Leu Leu Leu Val Ala Ala Pro Arg Trp
                -15                 -10                 -5

Val Leu Ser Gln Leu Gln Leu Gln Glu Ser Gly Pro Gly Leu Val Lys
         -1  1               5                   10

Pro Ser Glu Thr Leu Ser Leu Thr Cys Thr Phe Ser Gly Phe Ser Leu
```

```
                15                  20                  25
Ser Thr Asn Gly Met Gly Val Ser Trp Ile Arg Gln Pro Gly Lys
 30                  35                  40                  45

Gly Leu Glu Trp Leu Gly His Ile Tyr Trp Asp Glu Asp Lys Arg Tyr
                 50                  55                  60

Asn Pro Ser Leu Lys Ser Arg Val Thr Ile Ser Lys Asp Thr Ser Lys
                 65                  70                  75

Asn Gln Val Ser Leu Lys Leu Ser Ser Val Thr Ala Ala Asp Thr Ala
                 80                  85                  90

Val Tyr Tyr Cys Ala Arg Arg Ile Ile Tyr Asp Val Glu Asp Tyr
 95                 100                 105

Phe Asp Tyr Trp Gly Gln Gly Thr Thr Val Thr Val Ser Ser
110                 115                 120

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 20

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
         35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ser
                 85                  90                  95

Ser His Val Pro Leu Thr Phe Gly Gln Gly Thr Lys Leu Glu Ile Lys
                100                 105                 110

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 21

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Ser Leu Ser Thr Ser
                 20                  25                  30

Gly Met Ser Val Gly Trp Ile Arg Gln Ala Pro Gly Lys Gly Leu Glu
         35                  40                  45

Trp Leu Ala His Ile Trp Trp Asp Asp Lys Tyr Tyr Asn Pro Ser
 50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
```

```
                    85                  90                  95
Cys Ala Arg Arg Thr Thr Thr Ala Asp Tyr Phe Ala Tyr Trp Gly Gln
                100                 105                 110

Gly Thr Thr Val Thr Val Ser Ser
        115                 120

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 23

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Asp Lys Tyr Tyr Asn Pro Ser
    50                  55                  60

Leu Lys Ser Arg Phe Thr Ile Ser Lys Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
        115                 120
```

```
<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 26
```

```
Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 28
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45
```

```
Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 30
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95
```

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 31
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 32
<211> LENGTH: 121
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120

<210> SEQ ID NO 33

```
<211> LENGTH: 121
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120

<210> SEQ ID NO 34
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 35
```

```
Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 37
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45
```

```
Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 38

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95
```

```
Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 40

Gln Val Gln Leu Val Glu Ser Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Val Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 41

Gln Val Gln Leu Val Glu Ser Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 42
<211> LENGTH: 113
```

```
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (2)
<223> OTHER INFORMATION: Val or Ile
<220> FEATURE:
<221> NAME/KEY: MOD_RES
<222> LOCATION: (7)
<223> OTHER INFORMATION: Ser or Thr
<220> FEATURE:
<221> NAME/KEY: MOD_RES
<222> LOCATION: (14)
<223> OTHER INFORMATION: Thr or Ser
<220> FEATURE:
<221> NAME/KEY: MOD_RES
<222> LOCATION: (15)
<223> OTHER INFORMATION: Leu or Pro
<220> FEATURE:
<221> NAME/KEY: MOD_RES
<222> LOCATION: (30)
<223> OTHER INFORMATION: Ile or Val
<220> FEATURE:
<221> NAME/KEY: MOD_RES
<222> LOCATION: (50)
<223> OTHER INFORMATION: Arg, Gln, or Lys
<220> FEATURE:
<221> NAME/KEY: MOD_RES
<222> LOCATION: (88)
<223> OTHER INFORMATION: Val or Leu
<220> FEATURE:
<221> NAME/KEY: MOD_RES
<222> LOCATION: (105)
<223> OTHER INFORMATION: Gln or Gly
<220> FEATURE:
<221> NAME/KEY: MOD_RES
<222> LOCATION: (108)
<223> OTHER INFORMATION: Lys or Arg
<220> FEATURE:
<221> NAME/KEY: MOD_RES
<222> LOCATION: (109)
<223> OTHER INFORMATION: Val or Leu

<400> SEQUENCE: 42

Asp Xaa Val Met Thr Gln Xaa Pro Leu Ser Leu Pro Val Xaa Xaa Gly
1               5                   10                  15

Gln Pro Ala Ser Ile Ser Cys Arg Ser Ser Gln Ser Leu Xaa Tyr Ser
            20                  25                  30

Asp Gly Asn Ala Tyr Leu His Trp Phe Leu Gln Lys Pro Gly Gln Ser
        35                  40                  45

Pro Xaa Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Ser Gln Ser
                85                  90                  95

Thr His Val Pro Trp Thr Phe Gly Xaa Gly Thr Xaa Xaa Glu Ile Lys
            100                 105                 110

Arg

<210> SEQ ID NO 43
<211> LENGTH: 112
<212> TYPE: PRT
<213> ORGANISM: Artificial Sequence
<220> FEATURE:
<223> OTHER INFORMATION: Description of Artificial Sequence: Synthetic
      humanized antibody
```

```
<220> FEATURE:
<221> NAME/KEY: MOD_RES
<222> LOCATION: (1)
<223> OTHER INFORMATION: Glu or Gln
<220> FEATURE:
<221> NAME/KEY: MOD_RES
<222> LOCATION: (7)
<223> OTHER INFORMATION: Ser or Leu
<220> FEATURE:
<221> NAME/KEY: MOD_RES
<222> LOCATION: (46)
<223> OTHER INFORMATION: Glu, Val, Asp, or Ser
<220> FEATURE:
<221> NAME/KEY: MOD_RES
<222> LOCATION: (63)
<223> OTHER INFORMATION: Thr or Ser
<220> FEATURE:
<221> NAME/KEY: MOD_RES
<222> LOCATION: (75)
<223> OTHER INFORMATION: Ala, Ser, Val, or Thr
<220> FEATURE:
<221> NAME/KEY: MOD_RES
<222> LOCATION: (76)
<223> OTHER INFORMATION: Lys or Arg
<220> FEATURE:
<221> NAME/KEY: MOD_RES
<222> LOCATION: (89)
<223> OTHER INFORMATION: Glu or Asp
<220> FEATURE:
<221> NAME/KEY: MOD_RES
<222> LOCATION: (107)
<223> OTHER INFORMATION: Leu or Thr

<400> SEQUENCE: 43

Xaa Val Gln Leu Val Glu Xaa Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Xaa Leu Val
        35                  40                  45

Ala Gln Ile Asn Ser Val Gly Asn Ser Thr Tyr Tyr Pro Asp Xaa Val
    50                  55                  60

Lys Gly Arg Phe Thr Ile Ser Arg Asp Asn Xaa Xaa Asn Thr Leu Tyr
65                  70                  75                  80

Leu Gln Met Asn Ser Leu Arg Ala Xaa Asp Thr Ala Val Tyr Tyr Cys
                85                  90                  95

Ala Ser Gly Asp Tyr Trp Gly Gln Gly Thr Xaa Val Thr Val Ser Ser
            100                 105                 110

<210> SEQ ID NO 44
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 44

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Thr Tyr Cys Ser Gln Ser
                85                  90                  95

Thr His Val Pro Trp Thr Phe Gly Gln Gly Thr Lys Val Glu Ile Lys
            100                 105                 110

Arg

<210> SEQ ID NO 45
<211> LENGTH: 112
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Leu Val Thr Val Ser Ser
            100                 105                 110

<210> SEQ ID NO 46
<211> LENGTH: 219
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 46

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
```

```
                130             135             140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

<210> SEQ ID NO 47
<211> LENGTH: 442
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270
```

-continued

```
Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                     310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                     390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440
```